United States Patent
Birkholz et al.

(10) Patent No.: US 12,152,247 B2
(45) Date of Patent: Nov. 26, 2024

(54) NF-$_\kappa$B SIGNALING PATHWAY-MANIPULATED DENDRITIC CELLS

(71) Applicant: Friedrich-Alexander-Universität Erlangen-Nürnberg, Erlangen (DE)

(72) Inventors: Katrin Birkholz, Hohenschäftlarn (DE); Jan Dörrie, Nuremberg (DE); Niels Schaft, Weisendorf (DE); Gerold Schuler, Spardorf (DE); Reinhard Voll, Freiburg (DE); Isabell Pfeiffer, Munich (DE)

(73) Assignee: Friedrich-Alexander-Universität Erlangen-Nürnberg, Erlangen (DE)

( * ) Notice: Subject to any disclaimer, the term of this patent is extended or adjusted under 35 U.S.C. 154(b) by 104 days.

(21) Appl. No.: 17/871,680

(22) Filed: Jul. 22, 2022

(65) Prior Publication Data
US 2023/0151384 A1    May 18, 2023

Related U.S. Application Data

(60) Continuation of application No. 15/830,225, filed on Dec. 4, 2017, now Pat. No. 11,466,289, which is a division of application No. 13/881,592, filed as application No. PCT/EP2011/005400 on Oct. 26, 2011, now Pat. No. 9,862,968.

(30) Foreign Application Priority Data

Oct. 26, 2010   (EP) ..................... 10188893

(51) Int. Cl.
C12N 15/85     (2006.01)
A61K 35/12     (2015.01)
A61K 39/00     (2006.01)
C12N 5/0784    (2010.01)
C12N 9/12      (2006.01)

(52) U.S. Cl.
CPC ............ *C12N 15/85* (2013.01); *C12N 5/064* (2013.01); *C12N 9/1205* (2013.01); *A61K 2035/122* (2013.01); *A61K 2039/5154* (2013.01); *C12N 2501/70* (2013.01); *C12N 2510/00* (2013.01)

(58) Field of Classification Search
None
See application file for complete search history.

(56) References Cited

U.S. PATENT DOCUMENTS

2005/0059624 A1   3/2005   Hoerr et al.
2005/0059634 A1   3/2005   Venton et al.
2009/0202492 A1   8/2009   Beg et al.

FOREIGN PATENT DOCUMENTS

EP    1739186 A1      1/2007
WO    2007137300 A2   11/2007

OTHER PUBLICATIONS

Progress in Autoimmune Disease Research, 2005, pp. 1-124.*
Mor, 2005, J. Immunol. Vol. 175: 3439-3445.*
Appaiahgari et al., "Adenoviruses as gene/vaccine delivery vectors: promises and pitfalls," Expert Opin. Biol. Ther. (2015) 15(3):337-351.
Mossoba et al., "Cancer immunotherapy using virally transduced dendritic cells: animal studies and human clinical trials," Expert Rev Vaccines 5(5), pp. 717-732 (2006).
Wold et al., "Adenovirus Vectors for Gene Therapy, Vaccination and Cancer Gene Therapy," Curr Gene Ther. Dec. 2013, 13(6): 421-433.
Zhong et al., "Recombinant adenovirus is an efficient and non-perturbing genetic vector for human dendritic cells, " Eur. J. Immunol. 1999, 29: 964-972.
Delhase et al., "Positive and negative regulation of IkB kinase activity through IKKB subunit phosphorylation," Science Am. Ass. for the advancement of science; vol. 284, Apr. 1999; 309-313.
Mercurio, et al., 1997, Science vo. 278: 860-866.
Bonehill, et al., 2008, Mol. Ther. vol. 16:1170-80.
Li, et al., 2002, Nature Rev. vol. 2: 725-734.
Whisstock, et al., 2003, Quart. Rev. Biophy, vol. 36: 307-340.
Wang et al., 2001, J. Biol. Chem vol. 276: 49213-220.
Boczkowski, et al., "RNA as performance-ehancers for dendritic cells," Expert Opinion on Biological Therapy, Apr. 2010, pp. 563-574.
Kaisho, et al., "Turning Nf-KB and IRFs on and off in DC" Trends in Immunology, vol. 29, No. 7, Jun. 2008, pp. 329-336.
Aiello, et al., "DnIKK2-Transfected Dendritic Cells Induce a Novel Population of Inducible Nitric Oxide Synthase-Expressing CD4+ CD25– Cells with Tolerogenic Properties," Transplatation, vol. 83, No. 4, Feb. 27, 2007, pp. 474-484.
Tomasoni, et al., "Dendritic Cells Genertically Engineered with Adenoviral Vector Encoding dnIKK2 Induce the of Formation Potent CD4+ T-Regulaory Cells," Transplantation, vol. 79, No. 9, May 15, 2005, pp. 1056-1061.

* cited by examiner

*Primary Examiner* — Amy E Juedes
(74) *Attorney, Agent, or Firm* — Taft Stettinius & Hollister LLP

(57) ABSTRACT

The invention relates to dendritic cells, the NFκB signaling pathway of which has been manipulated by RNA transfection, to the manufacture thereof and to use thereof.

12 Claims, 15 Drawing Sheets

Specification includes a Sequence Listing.

NF-κB SIGNALING PATHWAY-MANIPULATED DENDRITIC CELLS

RELATED APPLICATIONS

This application is a divisional of U.S. patent application Ser. No. 13/881,592, filed on Sep. 9, 2013, which is a U.S. National Stage Application under 35 U.S.C. § 371 of International Application No. PCT/EP2011/005400, filed on Oct. 26, 2011, which claims priority to European Patent Application No. 10188893.1, filed on Oct. 26, 2010, the contents of which applications are incorporated by reference herein in their entirety.

SEQUENCE LISTING

The text file entitled "T3091_PCT_sequence_listing.txt," created on Aug. 11, 2017, having 68 kilobytes of data, and filed concurrently herewith, is hereby incorporated by reference in its entirety in this application.

FIELD OF THE INVENTION

The invention relates to dendritic cells, the NF$_K$B signaling pathway of which has been manipulated by RNA transfection, to the manufacture thereof and to use thereof.

BACKGROUND OF THE INVENTION

In the specification, reference is made to a number of documents from the prior art including patent applications and manufacturer's manuals. While the disclosure of these documents is not considered relevant to the patentability of the invention, it is incorporated by reference into the present specification.

Dendritic cells (DCs) are the link between the innate and the adaptive immune response. They are able to detect pathogens as such, and to initialize and direct an adaptive (that is, tailored to the specific pathogen) immune response. In the absence of pathogens, DCs are also capable of mediating tolerance against endogenous antigens. Thus, DCs are the key for the targeted induction of immune responses, but also for mediating immunological tolerance. The cytokine IL-12p70 plays an important role in the induction of cell mediated immunity, while the cytokine IL-10 is involved in the induction of humoral immunity, and also of tolerance. Immunotherapy of malignant diseases using DCs as adjuvants was tested already in various clinical trials, where the safety and feasibility of this method could be demonstrated. However, the clinical outcomes remained below expectations, although frequently the patients' immune responses against the antigens used were detectable in vitro. Generating the DCs in cell culture offers the opportunity to manipulate them in a targeted way. For this purpose, it is advantageous to generate DCs, which are able to induce long-lived memory T cells, and thereby act resistant to regulatory T cells (Tregs) and other tolerogenic mechanisms. Upon re-exposure to an antigen, long-lived memory T cells can mediate a more rapid and more efficient secondary response. This memory function can be provided by $CD4^+$ and $CD8^+$ memory T cells. Long-lived memory T cells are different from effector cells that only have a short life time and usually die after an immune response by activation-inducing cell death (AICD). Between the two cell types, however, there are transitional forms, such as the effector memory cells. Like effector cells, they are able to patrol throughout the body, and exert an effector function upon antigen contact, and they can proliferate and are also more long-lived than effector cells. On the other hand, the use of DCs for the targeted treatment of autoimmunity and allergies is conceivable because DCs can suppress immune responses and mediate tolerance under certain conditions. Improved methods and protocols for the manufacture of various types of DCs are therefore of great interest and are the object of research worldwide. An overview of the current prior art is presented in Boczkowski and Nair, Expert Opin. Biol. Ther. 10 (4) (2010), 563-574, and in Kaisho and Tanaka, Trends in Immunology 29 (7) (2008), 329-336. DCs have a variety of surface receptors with which they can identify various pathogens. In addition, DCs are able to perceive various endogenous messengers such as cytokines and chemokines, and surface molecules on other cells of the immune system. The DC processes the various incoming signals via intracellular signaling pathways, whereby various differentiation programs are triggered. The targeted manipulation of these signaling pathways may allow the creation of tailor-made DCs, which are thus better suited to mediate either immunity (in cancer immunotherapy) or tolerance (in the treatment of autoimmune diseases and allergies).

Different ways to intervene in the signaling pathways in the DC through genetic manipulation have already been formulated and implemented. However, various barriers get in the way, especially in the manipulation of human DCs. Genetic manipulation in the context of a therapy gives cause for concern, and somatic gene therapy is tightly regulated. In addition, the options of genetically modifying the human DCs most widely used in medicine (monocyte-derived DCs) are very limited, and only the use of viral transfection systems, which were developed from lentiviruses or adenoviruses, has been successful so far. The use of such vehicles for introducing DNA, however, has been viewed very critically, and bears additional risks. For example, by using lentiviruses, viral sequences are also always incorporated into the genome of the cell. This may destroy active endogenous genes, or the viral promoters may activate genes that would otherwise be inactive. Since integration into the genome is random, however, it is impossible to predict which genes may be affected. If tumor suppressor genes or oncogenes are destroyed or activated, the cell, in the worst case, may become a tumor cell. Also, the induced immune response may be directed against the viral products rather than against the desired antigens. The latter also applies to adenoviral systems, where, in this case, the immune response may be very severe, since many people already have an existing immune response against adenoviruses. In 1999, such a severe immune response against an adenoviral vector even resulted in a fatality.

A central signaling pathway of the DC is the NF$_K$B signaling cascade. Stimulation of many of the surface receptors of the DC leads to activation of this cascade, wherein inhibitory proteins are destabilized by phosphorylation, so that transcription factors will enter the nucleus where they cause the transcription of various genes. The kinases that perform such phosphorylation are called IKK (inhibitor of kappa kinases).

SUMMARY OF THE INVENTION

It has now been found that dendritic cells (hereinafter referred to as "DCs") can be manipulated in their NF$_K$B signaling pathway by RNA transfection and expression of mutant signal-transducing proteins of the NF$_K$B signaling pathway. Both constitutively active and dominant negative mutants were found. By the maturation of the DC prior to or after the RNA transfection, DCs with various phenotypes and cytokine profiles may be produced, with cytokines IL-12p70 (for induction of immunity) and IL-10 (for induction of tolerance or for generating immunosuppressed phenotypes) playing central roles. Thus, the invention relates to:

(1) Dendritic cells (DCs), the $NF_KB$ signaling pathway of which has been manipulated by RNA transfection with one or more nucleotide sequences encoding at least one mutant signal transducing protein of the $NF_KB$ signaling pathway;
(2) a method for the manufacture of $NF_KB$ signaling pathway manipulated DCs according to (1), comprising the RNA transfection of immature or mature DCs with one or more nucleotide sequences encoding a mutant signal transducing protein of the $NF_KB$ signaling pathway;
(3) a composition, pharmaceutical composition or drug comprising DCs according to (1);
(4) the use of the DC according to (1) for the stimulation of autologous $CD8^+$ T cells ex vivo;
(5) the use according to (1) for manufacturing a drug for the treatment and prevention of cancer and infectious diseases, such as HIV-mediated AIDS or autoimmune diseases in a patient; and to the same extent the DCs according to (1) for the treatment and prevention of cancer and infectious diseases or autoimmune diseases in a patient
(6) a process for the expansion of T cells, including the stimulation of autologous $CD8^m$ T cells ex vivo, comprising stimulating the cells with DCs according to (1); and
(7) a method for the treatment of cancer, infectious diseases or autoimmune diseases in a patient, comprising administering the DCs according to (1) to said patient.

Then, the DCs were electroporated without RNA with IKKa-EE-A16-RNA (activates alternative signaling pathway), IKKß-EEA10-RNA (activates classical signaling pathway) alone or in combination (15 ug of RNA each). 24 h after EP, the supernatants were collected and analyzed by an "inflammation cytometric bead array." The data from 3 independent donors are shown.

Figure 12:
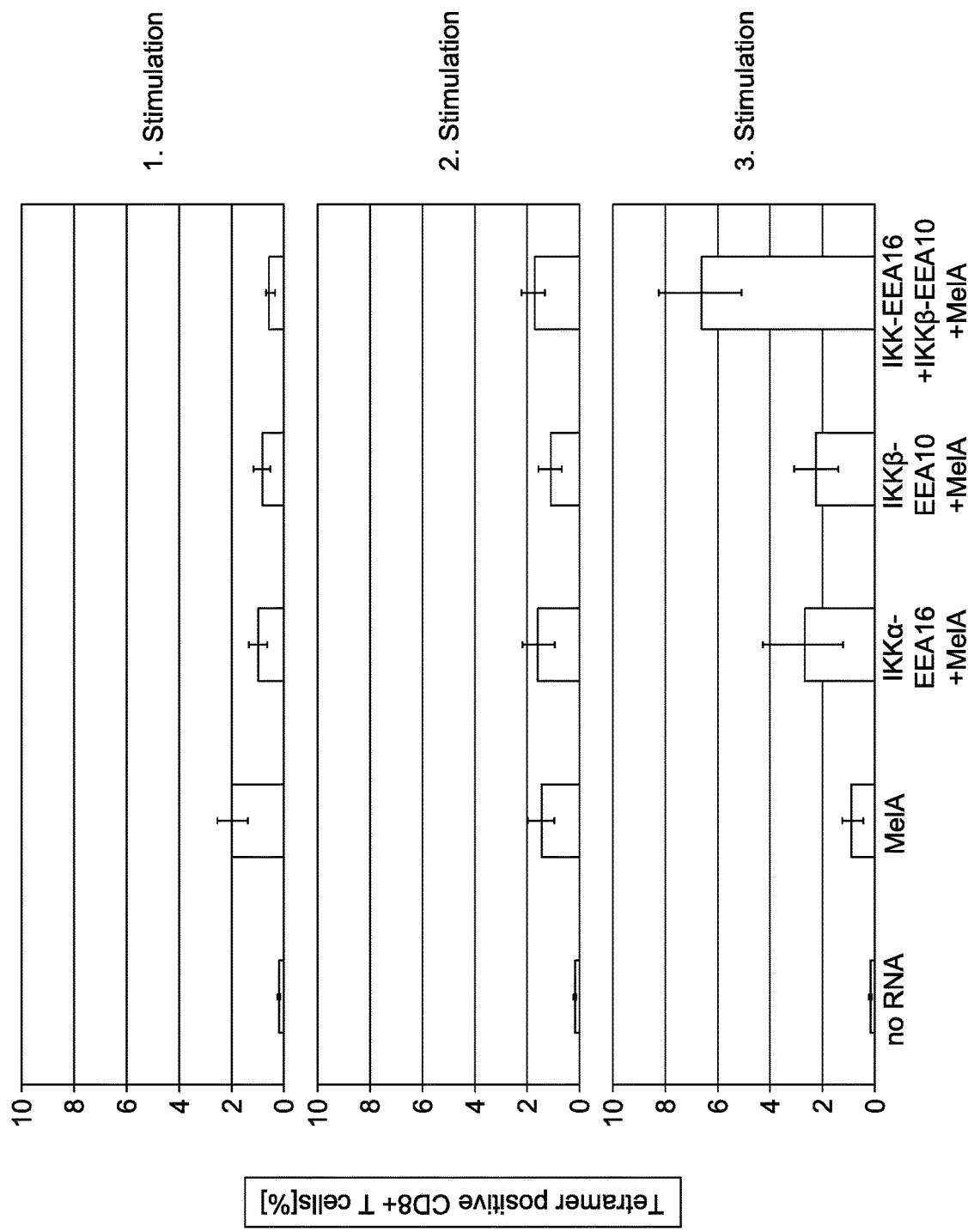

FIG. 12: Tetramer staining of the stimulation of autologous T cells with DCs, which were electroporated with RNA of components of the NFKB signaling pathway. Mature dendritic cells were electroporated without RNA, with IKKa-EE-A16-RNA (activates alternative signaling pathway), IKKß3-EEA10-RNA- (activates classical signaling pathway) alone or in combination (15 ug of RNA each). A portion of the DCs was coelectroporated with RNA encoding MelanA (MelA). 4 h after electroporation, autologous $CD8^+$ T cells were stimulated with these DCs in the ratio of 10:1. One week after the stimulation, the number of antigen-specific T cells was analyzed by tetramer staining, and the phenotype was identified by CCR7 and CD45RA staining. T cells were analyzed after an activating (1st stimulation) and two re-stimulations (2nd and 3rd stimulation). The mean of 5 independent donors is provided with the standard error of the mean.

Figure 13:
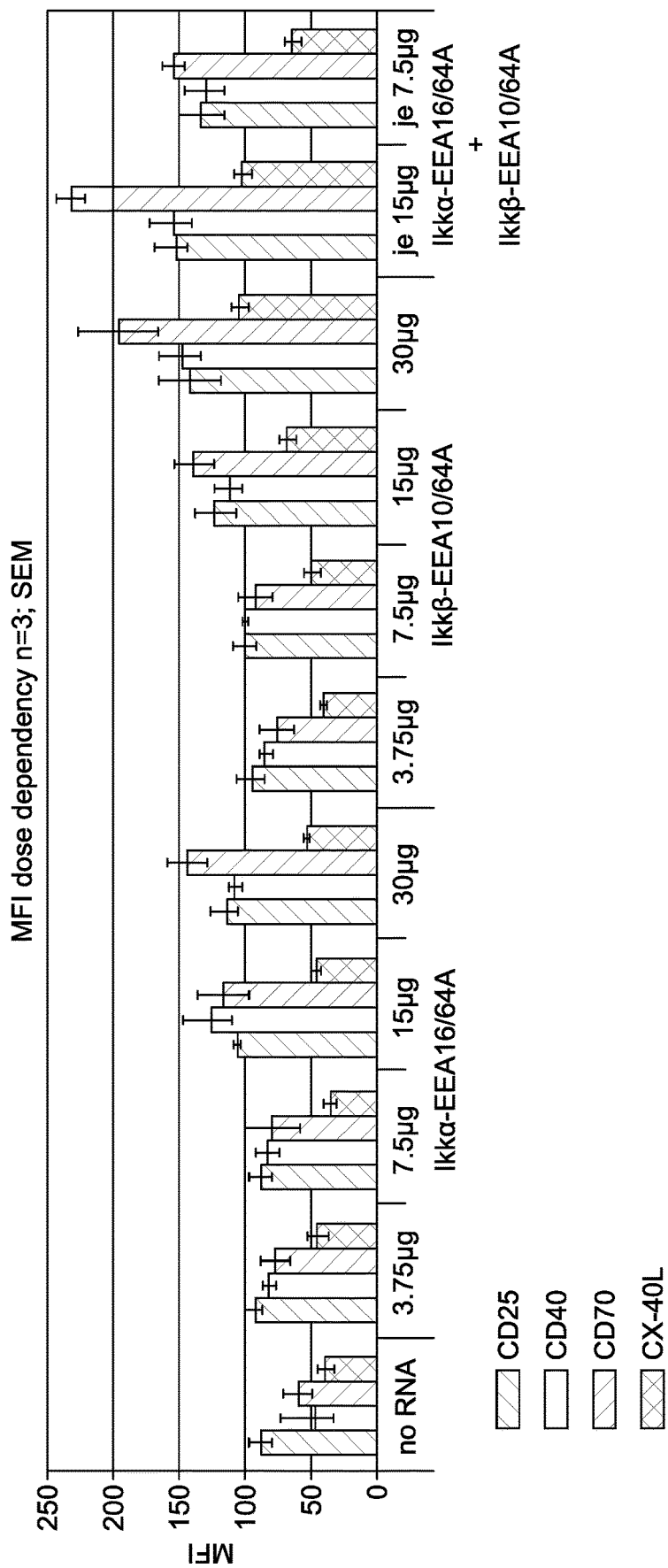

FIG. 13: Surface markers on DCs, which were electroporated with components of the NFKB signaling pathway with increasing concentrations of the transfected RNA. DCs were produced from monocytes during a six-day culture with GM-CSF and IL-4. On Day 6, the DCs matured for 24 h after addition of a standard maturation cocktail (IL-1ß, IL-6, TNFa and PGE2) (mDC). Then, the DCs were electroporated without RNA, with IKKa-EE-A16-RNA (activates alternative signaling pathway), IKKß-EEA10-RNA (activates classical signaling pathway) alone or in combination with increasing concentrations. These DCs were stained 24 h after EP with antibodies against CD25, CD 40, CD70, OX-40L, and analyzed by FACS. The mean of three independent donors is provided with the standard error of the mean.

Figure 14:
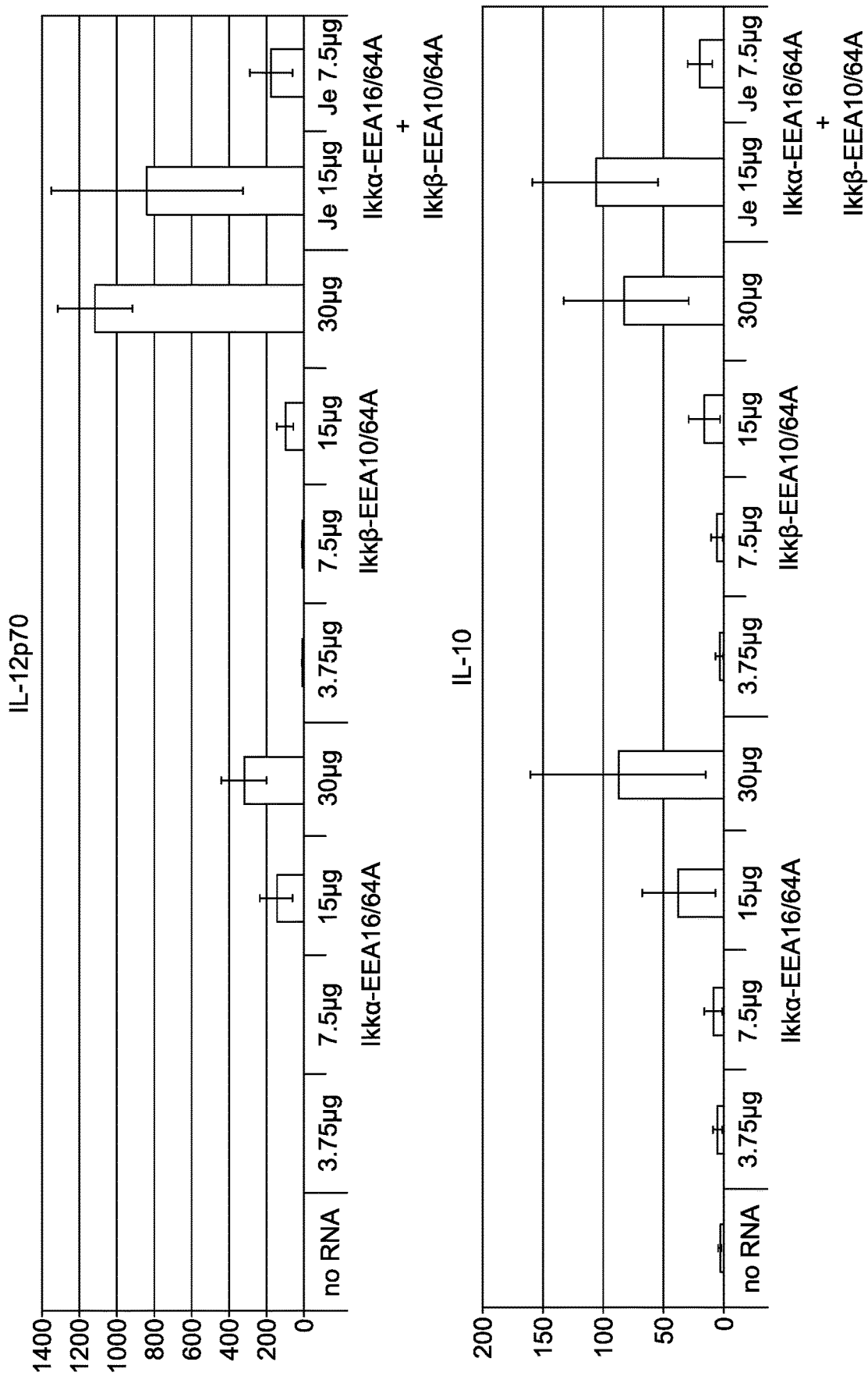

FIG. 14: Secretion of cytokines IL-12p70 and IL-10 by DCs, which were electroporated with components of the NFKB signaling pathway with increasing concentrations of the transfected RNA. DCs were produced from monocytes during a six-day culture with GM-CSF and TL-4. On Day 6, the DCs matured for 24 h after addition of a standard maturation cocktail (IL-1B, IL-6, TNFa and PGE2) (mDC). Then, the DCs were electroporated without RNA with IKKa-EE-A16-RNA (activates alternative signaling pathway), IKKß3-EEA10-RNA (activates classical signaling pathway) alone or in combination (with increasing concentrations). 24 h after EP, the supernatants were collected and analyzed by an "inflammation cytometric bead array." The mean of three independent donors is provided with the standard error of the mean.

Figure 15:
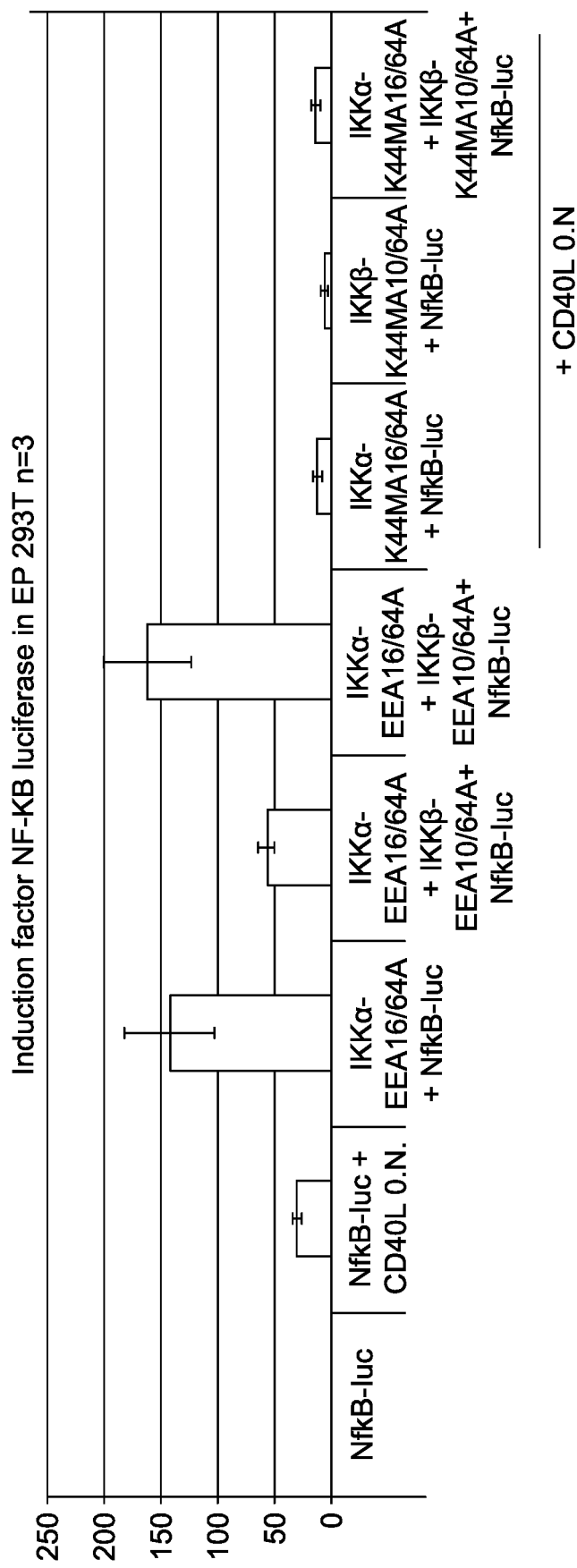

FIG. 15: Luciferase assay of 293T cells which were electroporated with components of NFKB signaling pathways. 293T cells were electroporated with activators (IKKa-EEA16-RNA or IKKß-EFA10-RNA) or inhibitors of the NFKB signaling pathway (IKKa-K44M-A16-A10-RNA or IKKß-K44M-A10-RNA) alone or in combination. All cells were coelectroporated with vectors encoding luciferase including an NFKB promoter. The NFKB signaling pathway of a portion of the cells was activated overnight with soluble CD40L. Luciferase activity was measured 24 hours after electroporation.

Figure 16:
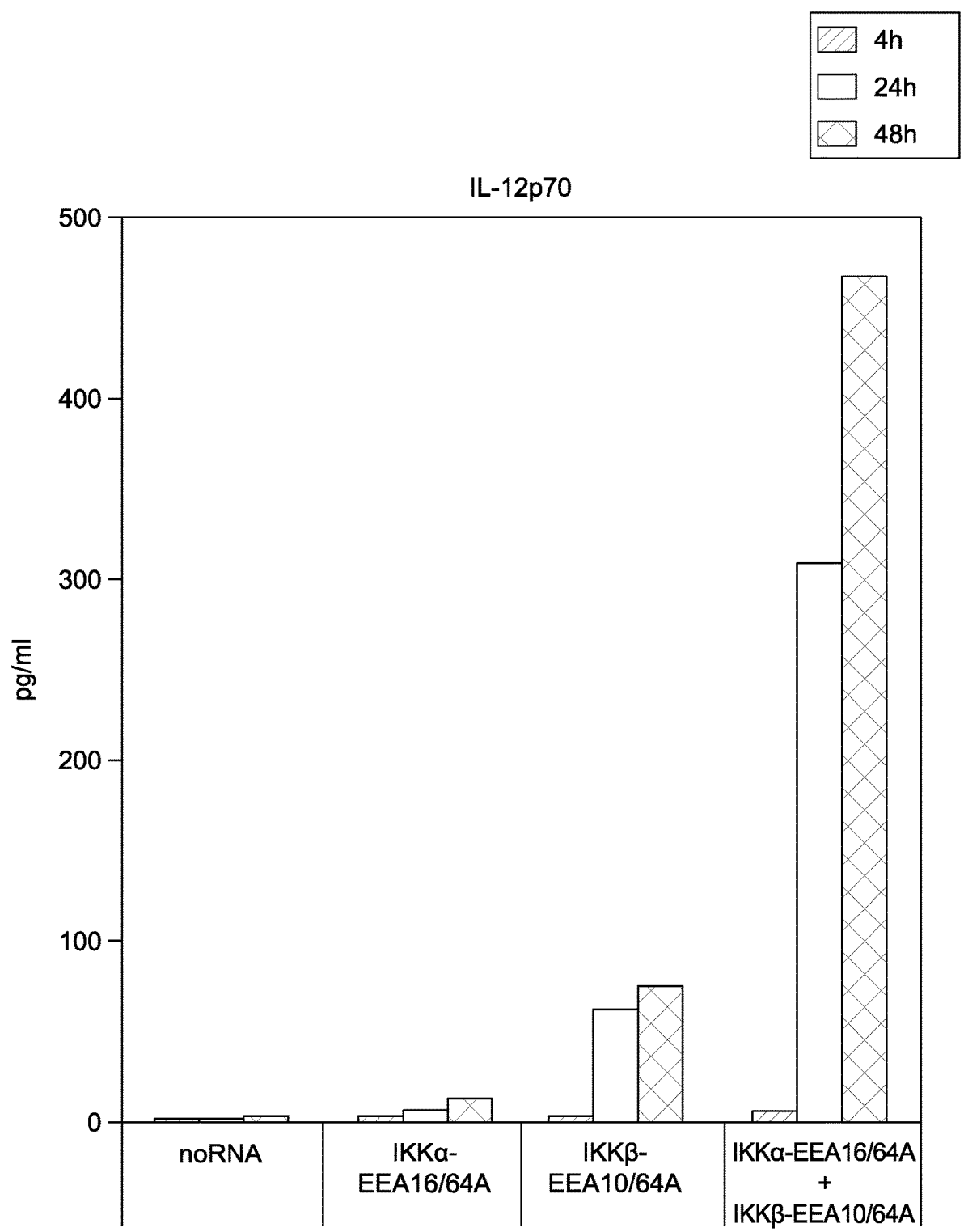

FIG. 16: Secretion of IL-12p70 by mature dendritic cells, which were transfected with RNA encoding constitutively active IKK mutants.

Figure 17:
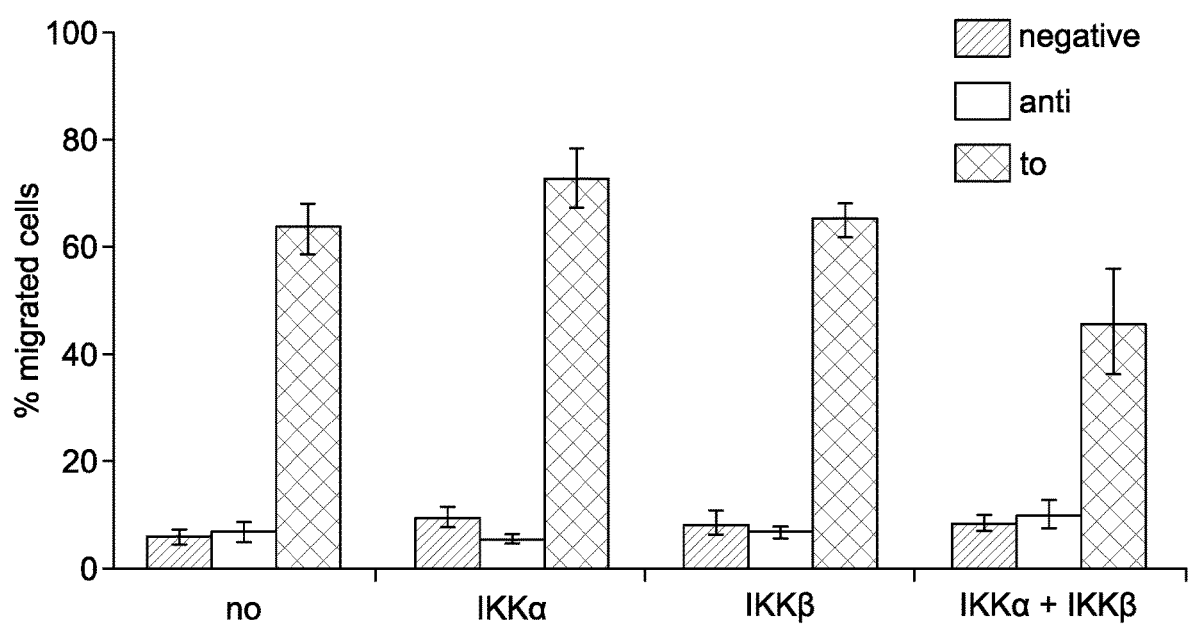

FIG. 17: Migration of mature dendritic cells which were transfected with RNA encoding constitutively active IKK mutants.

DETAILED DESCRIPTION OF THE INVENTION

The present invention relates to dendritic cells (DCs), the $NF_KB$ signaling pathway of which has been manipulated by RNA transfection with one or more nucleotide sequences encoding at least one mutant signal transducing protein of the $NF_KB$ signaling pathway. The invention further relates to dendritic cells, the $NF_KB$ signaling pathway of which has been manipulated by RNA transfection, to the manufacture thereof and to use thereof. It is based on the finding that DCs can be manipulated in their $NF_KB$ signaling pathway by RNA transfection and expression of mutant signal transducing proteins of the $NF_KB$ signaling pathway.

According to the invention, the term "dendritic cells" is used as in the prior art. In the immature state, they are characterized by low levels of MHC proteins and B7 co-stimulatory molecules, and the ability to phagocytosis and pinocytosis, and by the absence of the surface molecules CD83 and CD25. In the mature state, they are characterized by, inter alia, an altered pattern of cell surface proteins, wherein the surface expression of some or all of the following molecules is increased: CD25, CD40, CD70, CD80, CD83, CD86, and MHC proteins. "Mature" DCs are different from "immature" DCs, inter alia, in that the former are immunostimulatorily more active, usually retain the ability to migrate into the draining lymph nodes in vivo, and to present increasingly endogenously expressed and exogenous antigen in the MHC context. Under physiological conditions, only "mature" DCs are able to activate naive T cells.

According to the invention, the term "RNA transfection" is used as in the prior art. Accordingly, RNA transfection refers to introducing foreign RNA in a eukaryotic cell, a DC according to the invention, preferably a human DC. According to the invention, "nucleotide sequences" include DNA and RNA. Preferably, the RNA to be transfected is mRNA, which contains no introns. A definition of mRNA can be found in the prior art (see "Molekulare Genetik", Knippers, 9th revised edition, Thieme Verlag, 2006). The immunomodulatory efficiency of the DCs of the invention can be further increased by stabilizing the mRNA. This can take place, for example, by adding a cap analog during the in vitro transcription of the mRNA. The use of so-called ARCA ("anti-reverse cap analog") technology leads to a 100% correct orientation of the cap and therefore to a further increase in efficiency (Stepinski et al., RNA 7 (10), 2001, 1486-1495). Alternatively, the stability of the mRNA can be increased by attaching a cap structure enzymatically on the mRNA already synthesized in vitro, for example, as described in Tcherepanova et al., BMC Mol. Biol. (2008), 9:90. The stability of the mRNA can be further increased by attaching untranslated regions (UTR), such as of the ß-globin mRNA (cf., e.g., Yu et al., Mol. Cell Biol. 21(17) (2001), 5879-5888). An improvement in translation efficiency together with an expected improvement of the immunomodulatory properties of the DCs can also be achieved through the use of the capping methods described in the previous paragraph, as well as by known methods such as the insertion of an "internal ribosome entry site" (IRES) at the 5' end of the in vitro translated RNA (Tan et al., Hum.

Immunol. 69(1), 2008, 3240). The translated protein yield in transfection experiments can be increased generally and so also in the context of the present invention, by extending the length of the polyA tail. This technology leads to even better results if it is applied together with the ARCA technology (hockey et al. Biochem. Biophys. Res. Commun. 340(4) (2006), 1062-1068). In relation to the present invention, a "mutant signal transducing protein of the $NF_KB$ signaling pathway" is defined as a protein, which is a component of the known signal cascade that leads to activation of $NF_KB$ and the subsequent translocation of this protein into the cell nucleus. According to the invention, this term encompasses further proteins that interact in a modulatory manner with components of the signal cascade and influence its activity. Compared with corresponding wild-type proteins, all of these proteins have changes (mutations). The corresponding mutations are defined, inter alia, by deletions, extensions or, preferably, the substitution of one or more amino acids.

In relation to the present invention, the definition of the $NF_KB$ signaling pathway comprises the classical and the alternative signaling pathway. The classical signaling pathway is activated by microbiological and viral infections or by cytokines. In this context the IKK complex consisting of IKKα, IKKß and NEMO induces the degradation of I-KB by phosphorylation, whereupon the transcription factor $NF_KB$ translocates into the cell nucleus and activates various target genes. The alternative $NF_KB$ signaling pathway is independent of IKKß and NEMO. Here, IKKα interacts with p100 ($NF_KB2$) that is processed into its p52 shape and together with RelB translocates into the cell nucleus and activates target genes. "Manipulations" of the $NF_KB$ signaling pathway with respect to the present invention can be measured by a change in activity of dendritic cells. This includes changes in the secretion of IL12p70, the secretion of IL-10, the migration or the expression of various induction factors, such as OX-40L or CD25. Preferably encompassed is the (increased) secretion by dendritic cells transfected with constitutively active mutants of IKKα and/or IKKß, of IL12p70 at preferably at least 5-fold, more preferably at least 10-fold, even more preferably at least 30-fold, and most preferably at least 50-fold increased levels compared with dendritic cells transfected with control RNA or non-transfected dendritic cells, which preferably are mature dendritic cells. Furthermore, preferred is the secretion of IL-10 at at least 5-fold, more preferably at least 10-fold and most preferably at least 30-fold increased levels by dendritic cells, preferably immature dendritic cells preferably transfected with constitutively active mutants of IKKα and/or IKKß and are compared with untransfected or control RNA-transfected dendritic cells. Preferred may be also a high IL-12p70 secretion in conjunction with low IL-10 secretion at a ratio of IL-12p70 to IL-10 of preferably at least 3, more preferably at least 5, even more preferably at least 10 and most preferably at least 20, by preferably mature dendritic cells transfected with constitutively active mutants of IKKα and/or IKKß.

Figure 1:
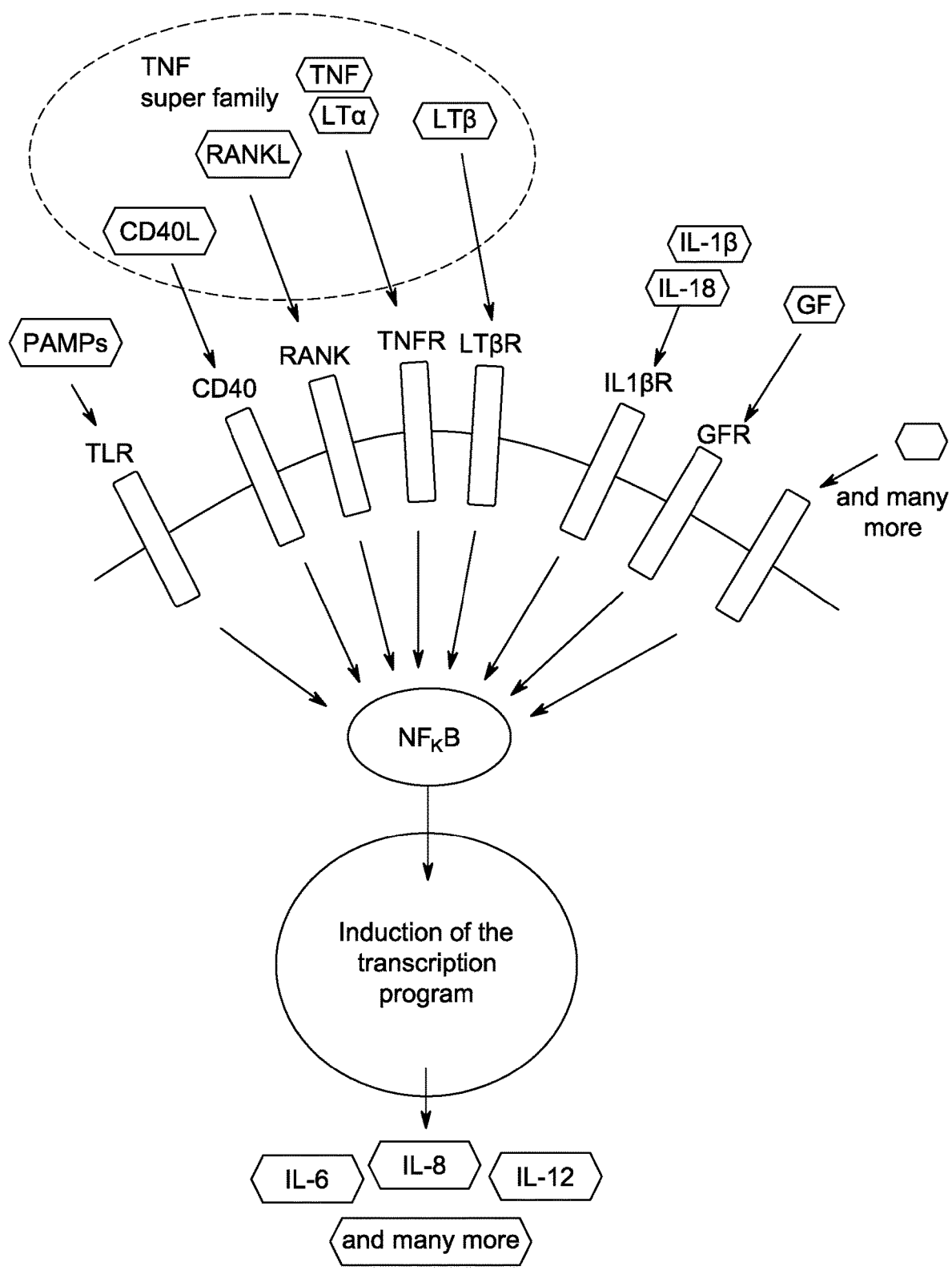
FIG. 1: NFKB is at the center of the DC maturation signal chain. A variety of surface receptors that are triggered by danger signals, and proinflammatory stimuli, which are known to trigger DC maturation, cause activation of NFKB. NFKB activation in turn causes the release of important cytokines such as IL-12p70 and phenotypic changes of the DCs.
Figure 2A:
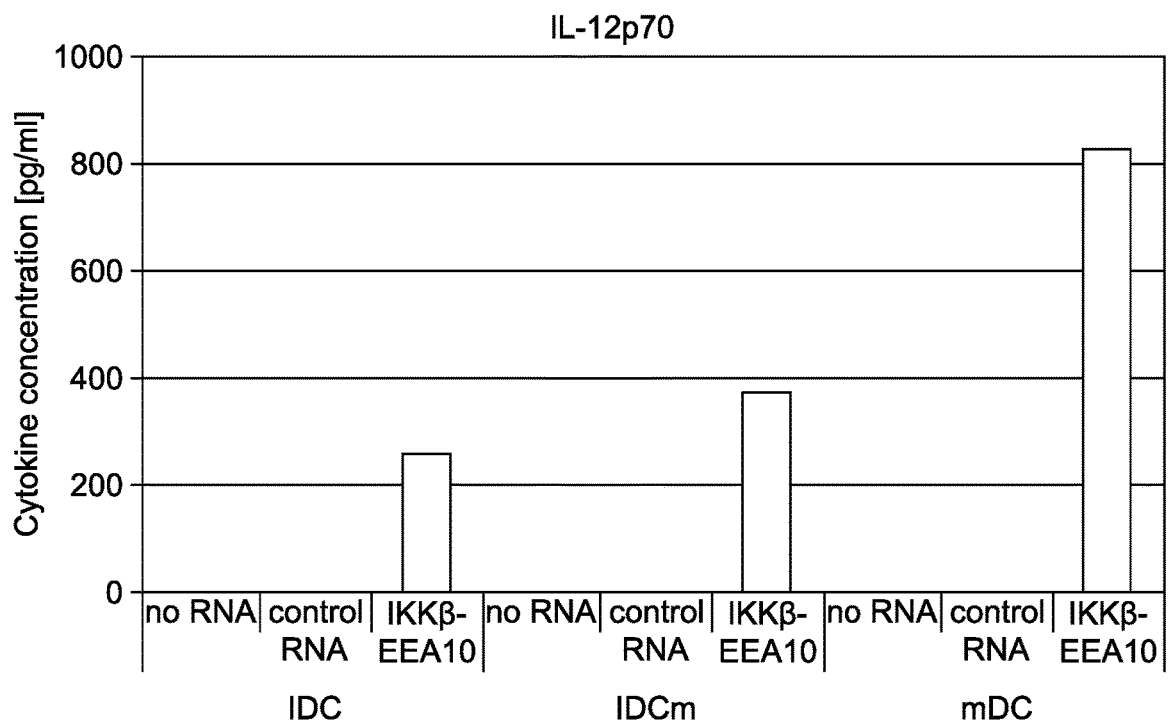
FIG. 2a depicts the secretion of IL-12p70 and IL-10 (FIG. 2b) by IKKß-EEA10-RNA electroporated dendritic cells.

Via RNA transfection of dendritic cells, the inventors were able to demonstrate in the present invention, surprisingly, that dendritic cells modified by RNA transfection can be manipulated in their function via the $NF_KB$ signaling pathway. The RNA transfection of various RNAs into dendritic cells can lead to either immunostimulation or tolerance induction or suppression of immunological responses. Transfected RNAs may enhance the secretion of IL-12p70, and thus lead to an immunostimulation. A further surprising effect of the present invention is based on the fact that identical RNAs, such as RNAs encoding constitutively activating mutants of IKKα and IKKß, have different effects on the immunostimulation of dendritic cells, depending on the time of their RNA transfection (see FIGS. 2a and 2b). According to the invention, immunostimulation is observed in transfection of mature DCs with RNAs, the transcription of which results in proteins in which the serine residues that are phosphorylated at physiological activation of IKK and thereby mediate the kinase activity of IKK, are replaced by glutamine residues. This allows, for example, in simultaneous presentation of tumor antigens by the DC, an effective killer T cell activation to be achieved, which can be exploited in the patients in combating tumors after administration of the transfected (autologous) DCs. This principle can be applied accordingly in other diseases. By contrast, if the RNA transfection is performed with immature DCs, according to the invention, an immunosuppressive effect is expected, since such DCs secrete large amounts of the immunosuppressive IL-10. Both alternatives represent preferred embodiments of the invention. Surprisingly, it was also shown that mature DCs of the invention are capable of migration (see FIG. 5). Such control of the immunological activity of dendritic cells is a major advance for medical use, for example in the form of vaccination with dendritic cells for the treatment of cancer patients.

According to the invention, said immunomodulatory, especially antigen-presenting, properties of the DCs can be further enhanced when, in addition to the RNA encoding said mutant signal-transducing protein(s), inhibitory RNAs such as siRNAs are introduced into the DCs or expressed there to inactivate mRNAs encoding immunosuppressive proteins such as, inter alia, A20, IL-10, TGF. Such a method is described in Breckpot et al. J. Immunol. 182(2) (2009), 860-870. A higher, more efficient induction of antigen-specific cytolytic activity by the DCs as an antigen presenting cell is also expected when immune-proteasome mRNA is inactivated therein, for example by siRNAs (Dannull et al., Blood 110(13) (2007), 4341-4350). An enhanced effect of DC-mRNA vaccines, for example in the fight against cancer, is also expected after stimulation of the DCs by single- or double-stranded RNA sequences (cf, e.g., Diebold et al., Science 303 (2004), 1529-1531).

Suitable preferred mutant signal-transducing proteins of the $NF_KB$ signaling pathway are mutants of the inhibitor of kappa kinases IKK, preferably constitutively active IKKα or IKKß mutants, or IKKα or IKKß inhibitory mutants. For the manufacture of the DCs according to aspect (1) of the invention several constitutively active or dominant-negative mutants of different IKKs have been manufactured experimentally. In this context, constitutively active IKKα and IKKß mutants are preferably those which, starting from the corresponding wild-type sequences, preferably from SEQ ID NO:1 and 4, respectively, have one or more substitutions of Ser by Glu in the active site. Preferred are such IKKα a mutants in which one or more of the amino acid residues Ser176 and Ser180 of the IKKα wild-type of SEQ ID NO:1 is replaced by Glu, particularly preferably amino acid residues Ser176 and Ser180 of the IKKα wild-type of SEQ ID NO:1 are replaced by Glu, and optionally one or more of the destabilizing C-terminal serine and threonine residues, preferably destabilizing serine and threonine residues at positions 661, 662, 665, 669, 670, 676, 679, 680, 686, 687, 693, 695, 699, 705, 706, 721 and 722, and in a less preferred form 661, 662, 665, 669, 670, 676, 679, 680, 686, 687, 692, 694, 698, 704 and 705 of the wild-type of SEQ ID NO:1 are replaced by alanine residues. All mentioned IKK mutants, which are characterized by the insertion of alanine residues, lead to a stabilization of the protein and are furthermore characterized in that they enhance the effect of increased or inhibitory activity, respectively. In addition, in all embodiments of the invention, the introduction of the stabilizing alanine residues into the proteins represents preferred embodiments. Preferably, at least two, preferably at least three, more preferably at least four, more preferably at least eight, and particularly preferably all of said residues are replaced by alanine residues. According to the invention all possible permutations, even if they are not mentioned here, are explicitly included in the disclosure of this specification as if they were specified individually herein. Furthermore, those IKKß mutants are preferred, in which one or more of the amino acid residues Ser177 and Ser181 of the IKKß wild-type, preferably of SEQ ID NO:4, are replaced by Glu, particularly preferably the amino acid residues Ser177 and Ser181 of the IKKß wild-type of SEQ ID NO:4 are replaced by Glu, and optionally one or more of the C-terminal destabilizing serine und threonine residues, preferably those destabilizing serine und threonine residues at positions 670, 672, 675, 679, 682, 689, 692, 695, 697 and 705 of the wild-type of SEQ ID NO:4 are replaced by alanine residues.

Particularly preferred are those constitutively active IKKα and IKKß mutants comprising the amino acid residues 25 to 769 of SEQ ID NO:2 or the amino acid residues 18 to 773 of SEQ ID NO:5, preferably having the sequence of SEQ ID NO:2 or SEQ ID NO:5, or wherein the coding RNA sequence contains SEQ ID NO:3 or 6. Furthermore, each mRNA, which contains a sequence which may originate by silent mutations from sequence SEQ ID NO:3 or 6, as by, inter alia, codon optimization, is encompassed in the disclosure of this specification.

In this context, the inhibitory IKKα and IKKß mutants are those which, starting from the corresponding wild-type sequences of SEQ ID NO:1 or 4, have a substitution of Lys by Met. Here, such IKKα mutants are preferred in which the amino acid residue Lys44 of the IKKα wild-type of SEQ ID NO:1 is substituted by Met, and optionally one or more of the destabilizing C-terminal serine und threonine residues, preferably destabilizing serine and threonine residues at positions 661, 662, 665, 669, 670, 676, 679, 680, 686, 687, 693, 695, 699, 705, 706, 721 and 722 of the wild-type of SEQ ID NO:1 are replaced by alanine residues. Further, such IKKß mutants are preferred in which the amino acid residue Lys44 of the IKKß wild-type of SEQ ID NO:4 is replaced by Met, and optionally one or more of the destabilizing C-terminal serine and threonine residues, preferably those destabilizing serine und threonine residues at positions 670, 672, 675, 679, 682, 689, 692, 695, 697 and 705 of the wild-type of SEQ ID NO:4 are replaced by alanine residues.

Particularly preferred are such inhibiting IKKα and IKKß mutants comprising the amino acid residues 24 to 768 of SEQ ID NO:7 or the amino acid residues 24 to 779 of SEQ ID NO:9 and preferably having the sequence of SEQ ID NO:7 or SEQ ID NO:9, or having the RNA sequence of SEQ ID NO:8 or 10, or the RNA sequence of which can be converted by silent mutations in the RNA sequence of SEQ ID NO:8 or 10.

Another particularly preferred embodiment, as mentioned above, relates to dendritic cells of the invention, wherein the DCs (i) are mature DCs; and/or (ii) are $NF_{\kappa}B$-activated DCs producing IL-12p70; and/or (iii) are $NF_{\kappa}B$-activated DCs producing IL-10; and/or (iv) are also loaded with one or more target antigens.

In the present invention, the definition of "target antigen" includes peptide chains that are attached to the major histocompatibility complex (MHC), for example, and are presented on the cell surface of dendritic cells, T cells. They can be derived, inter alia, from a tumor antigen such as MelanA, GP100, members of the MAGE family, but also mutant tumor antigens such as BRAF-V600E and GNAQ-Q209L. But sources of non-defined antigens can also be used, such as tumor lysate or mRNA isolated from the tumor. Also, any viral protein may be an antigen source, such as HIV-1 NEF or influenza matrix protein.

The above-mentioned mutants may be expressed in DCs by RNA transfection of corresponding mRNA molecules. The RNA transfection is not a genetic change of the DCs, and is thus safe from a clinical point of view. Following the transfection of DCs with a constitutively active IKK mutant, after having been incubated with cytokines IL-1ß, IL-6, TNFα and PGE2 ("matured"), they started to secrete the proinflammatory cytokine IL-12p70 (FIG. 2a), which is thought to play a crucial role in the induction of robust, long-lasting immune responses. Regarding the maturation of DCs, in addition to IL-1beta, IL-6, TNF and PGE2, alternatively or in addition, other substances may be used for maturation of DCs, including but not limited to: IFN-alpha, -beta, -gamma, artificial and natural TLR agonists, such as, inter alia, polyLC, CpG, LPS, flagellin, or soluble and surface-bound substances that specifically bind surface receptors of the DCs.

Figure 2B:
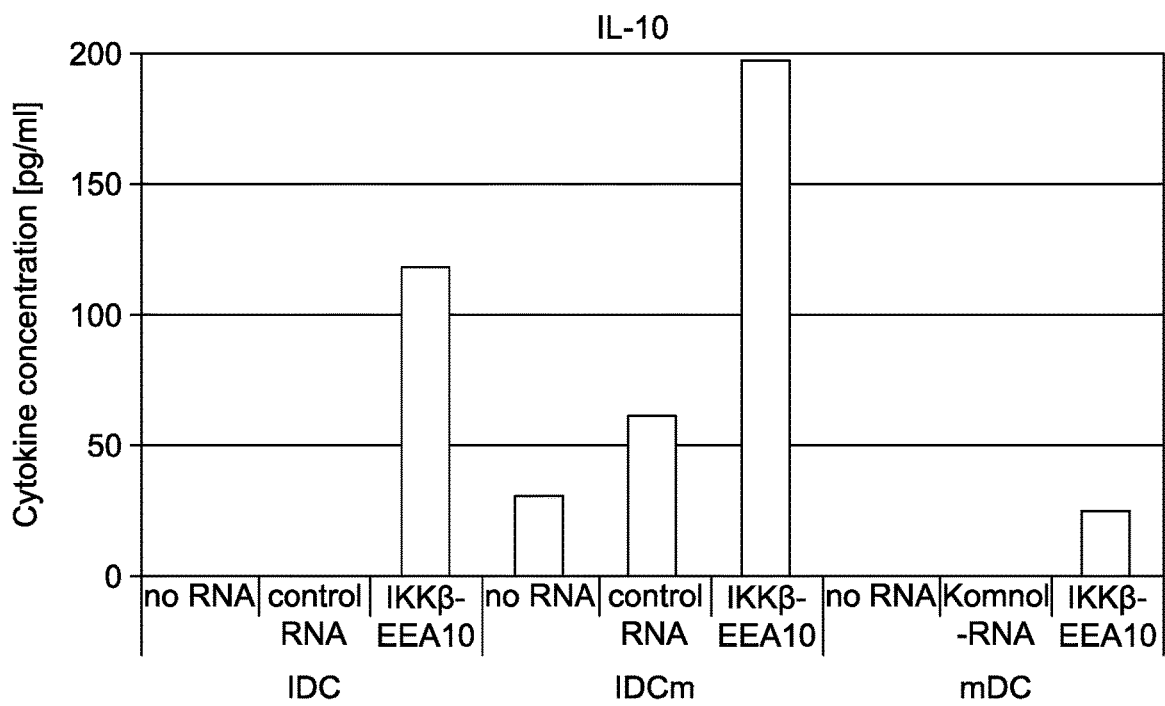
Figure 3:
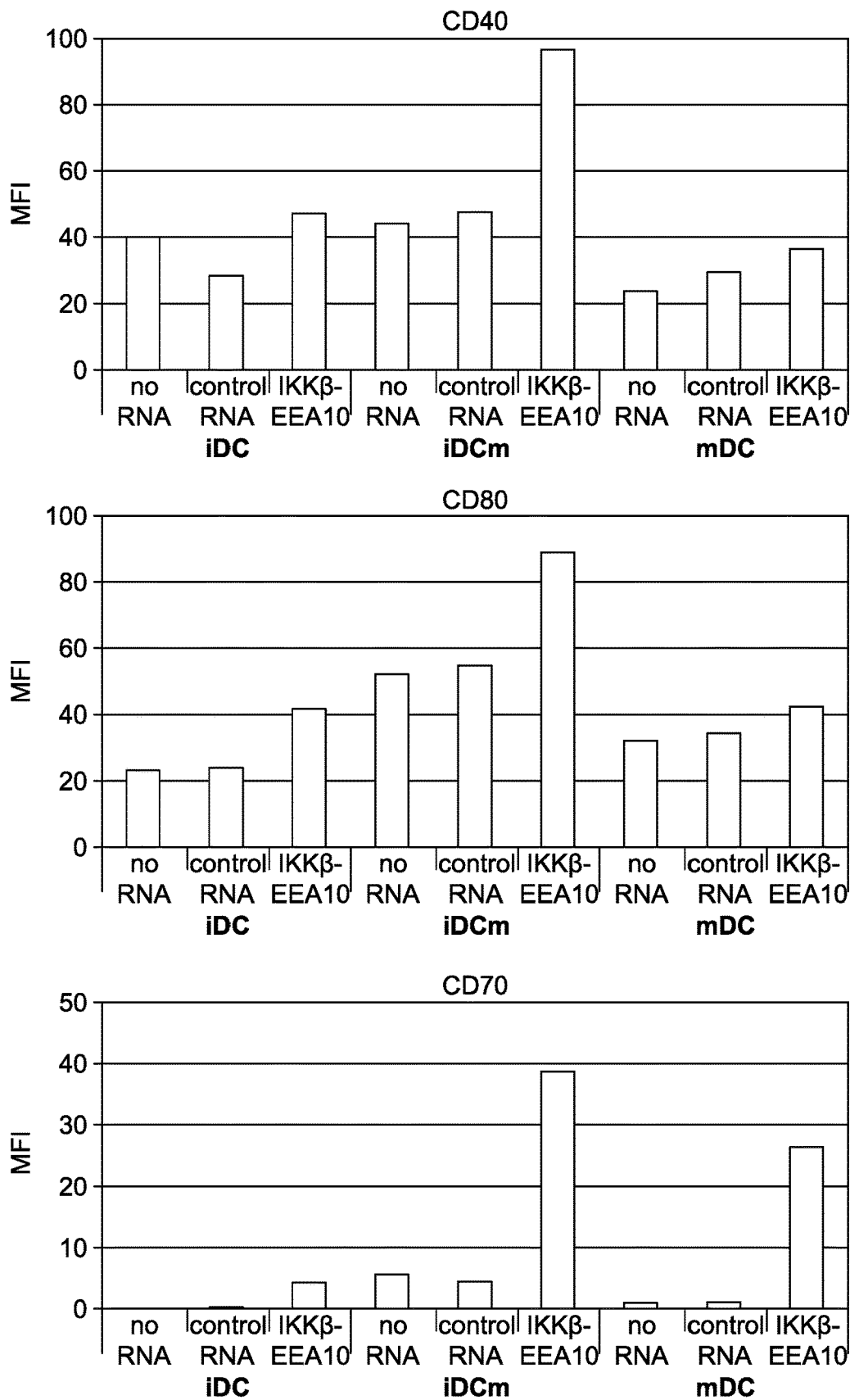
FIG. 3: Expression of surface markers on dendritic cells, transfected with the NFKB signaling component IKKß-EEA10.
Figure 4A:
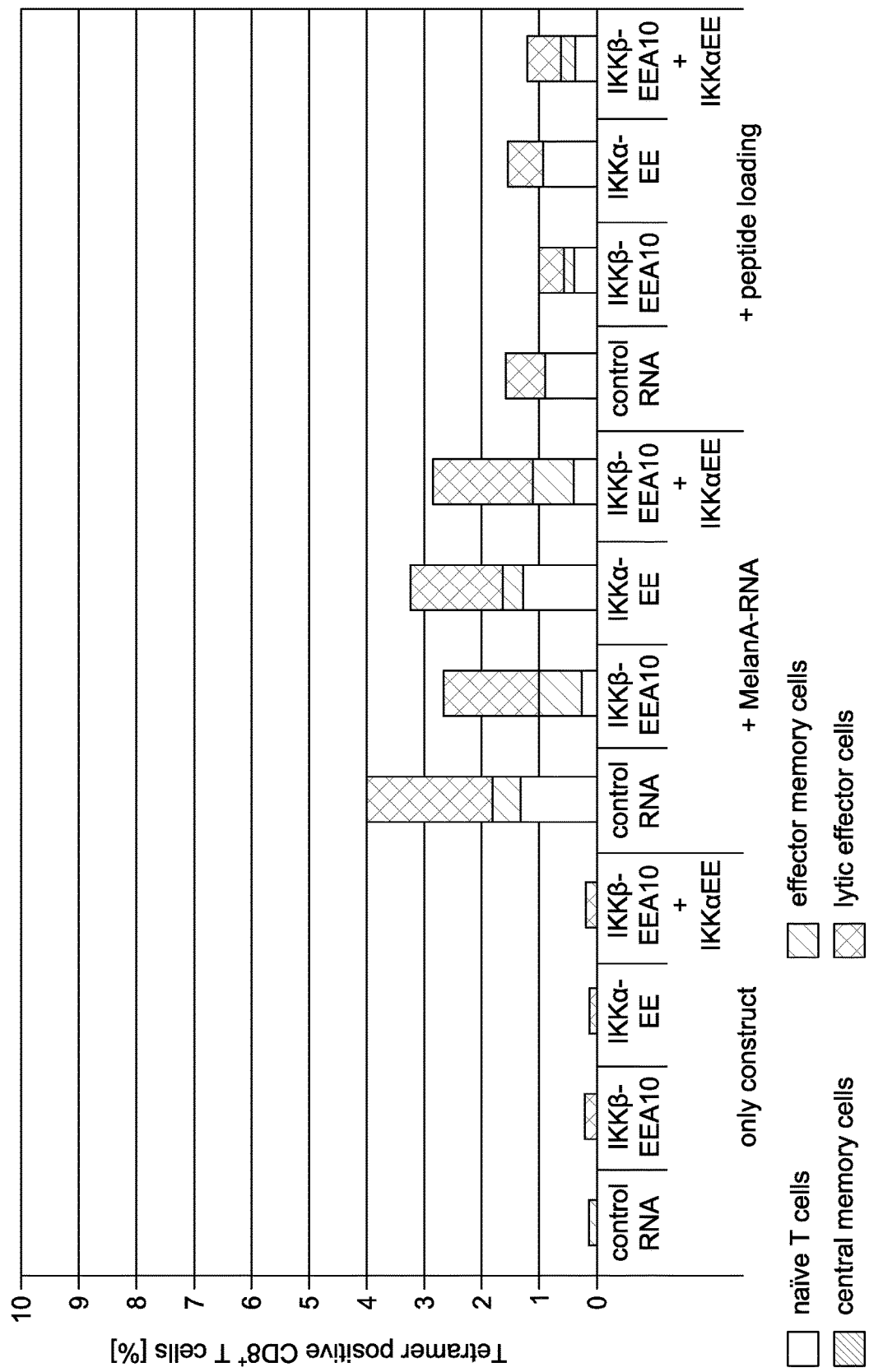
FIG. 4a,b depicts tetramer staining of the stimulation of autologous T cells with dendritic cells, electroporated with one or two RNAs encoding constitutively activated mutants of IKKα and IKKß, and analyzed after a priming (FIG. 4a) and after a restimulation (FIG. 4b).
Figure 4B:
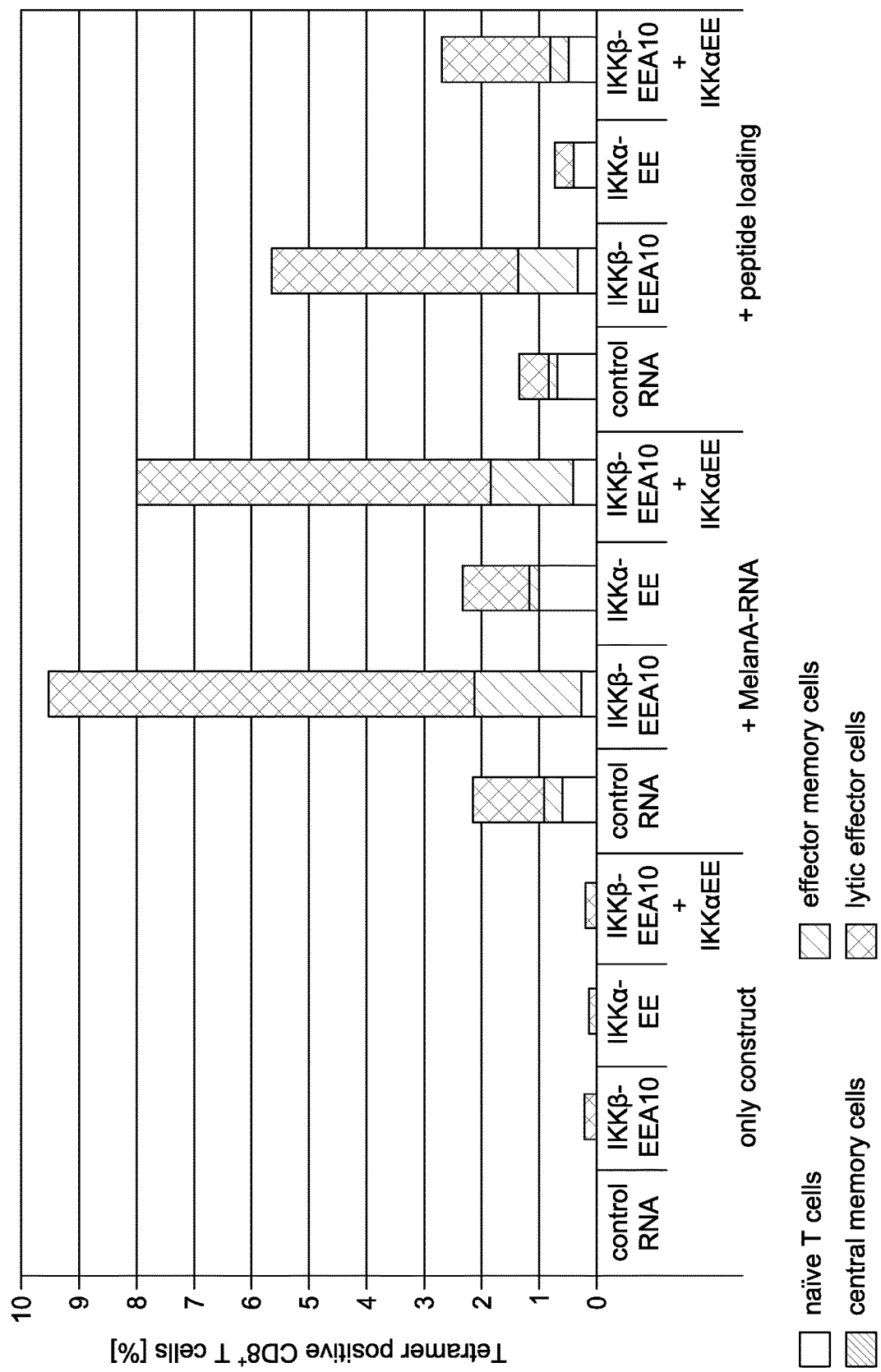
Figure 5:
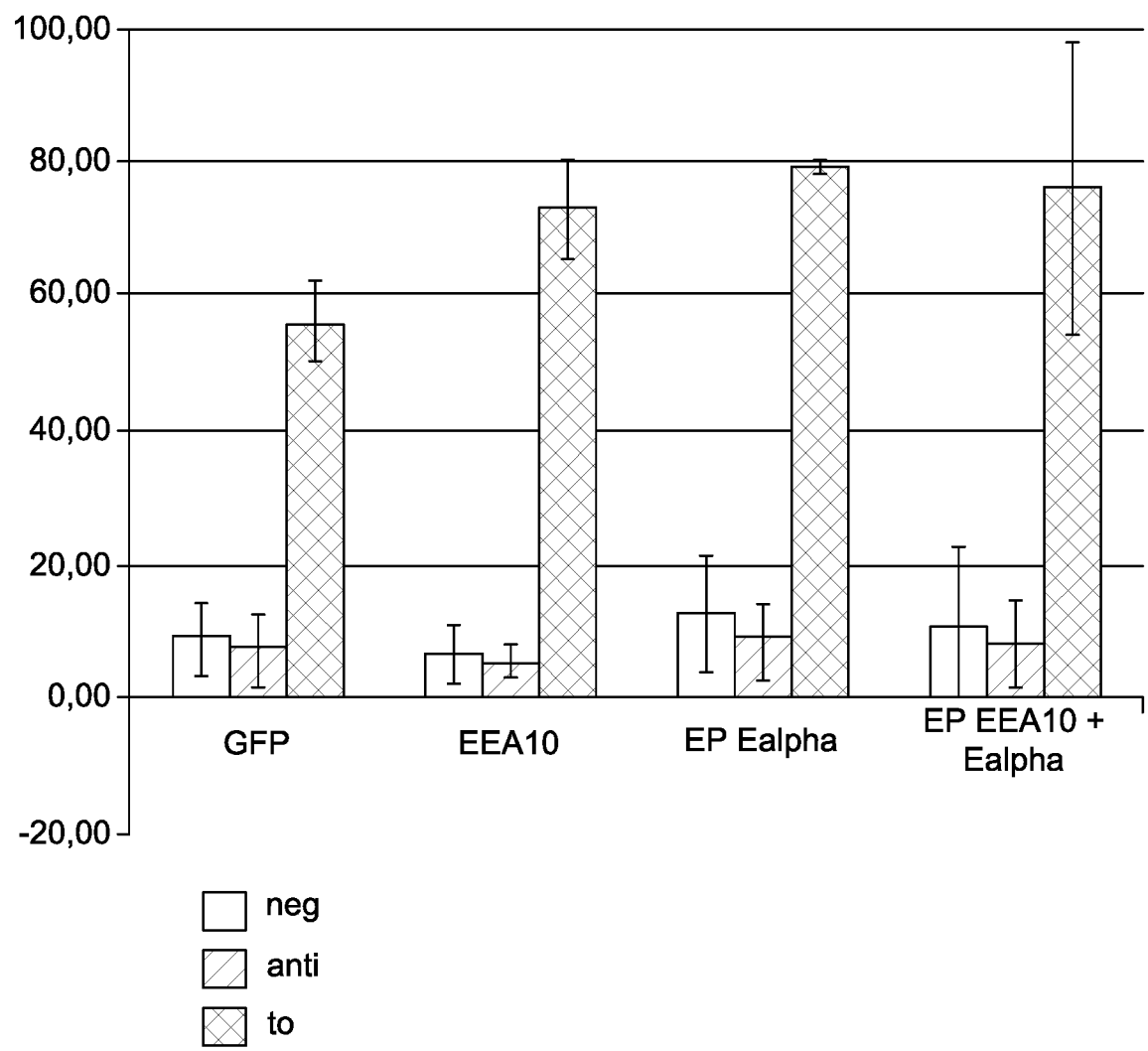
FIG. 5: Migration of mature dendritic cells 24 h after RNA transfection with one or two RNAs encoding constitutively activated mutants of IKKα and IKKI3.
Figure 6:
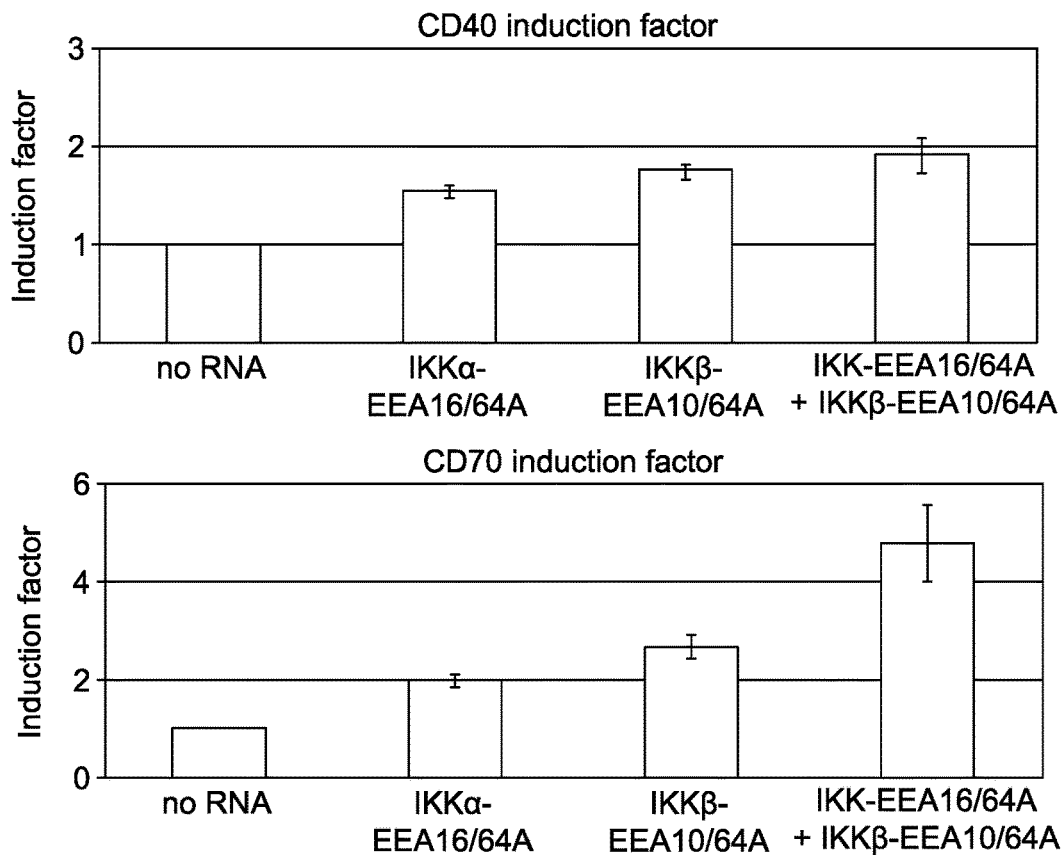
FIG. 6: Induction factor of surface markers on DCs, which were electroporated with components of the NFKB signaling pathway. DCs were produced from monocytes during a six-day culture with GM-CSF and IL-4. On Day 6, the DCs matured for 24 h after addition of a standard maturation cocktail (IL-1ß, IL-6, TNFa and PGE2) (mDC). Then, the DCs were electroporated without RNA, with IKKa-EE-A16-RNA (activates alternative signaling pathway), IKKß-EEA10-RNA (activates classical signaling pathway) alone or in combination (15 ug of RNA each). These DCs were stained 24 h after EP with antibodies against CD 40 and CD70, and analyzed by FACS. The mean of 8 independent donors is provided with the standard error of the mean.
Figure 7:
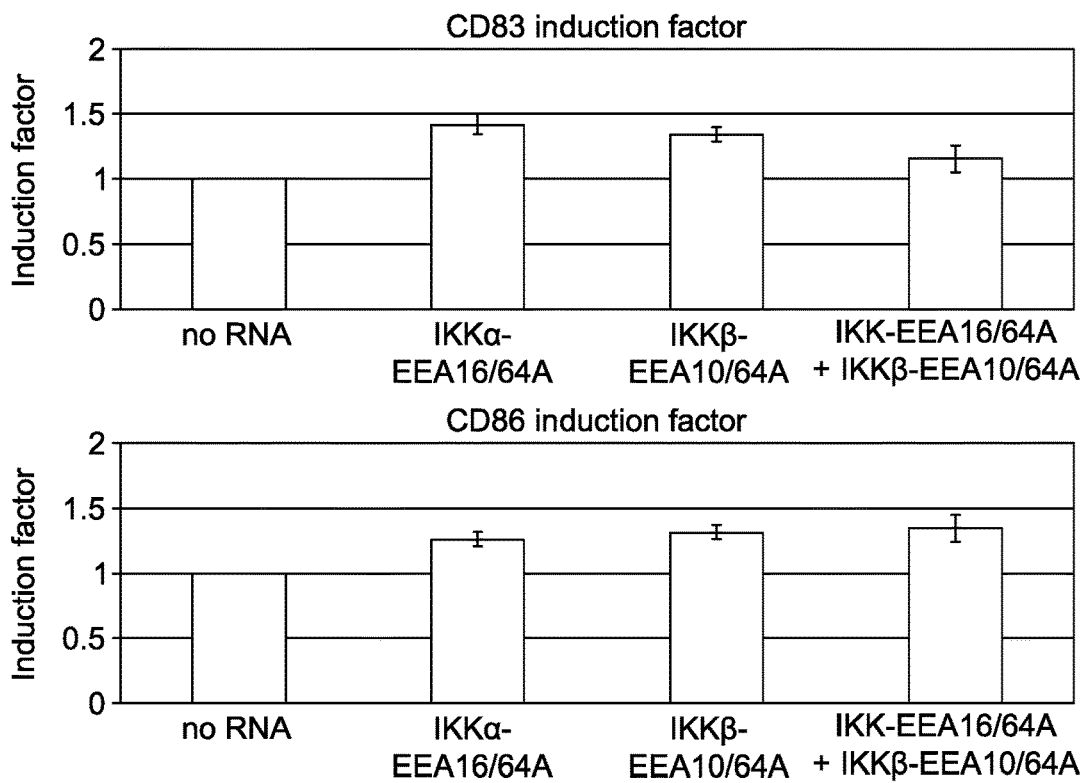
FIG. 7: Induction factor of surface markers on DCs, which were electroporated with components of the NFKB signaling pathway. DCs were produced from monocytes during a six-day culture with GM-CSF and IL-4. On Day 6, the DCs matured for 15 24 h after addition of a standard maturation cocktail (IL-1ß, IL-6, TNFa and PGE2) (mDC). Then, the DCs were electroporated without RNA, with IKKa-EE-A16-RNA (activates alternative signaling pathway), IKKß3-EEA10-RNA (activates classical signaling pathway) alone or in combination (15 ug of RNA each). These DCs were stained 24 h after EP with antibodies against CD83 and CD86, and analyzed by FACS. The mean of 8 independent donors is provided with the standard error of the mean.
Figure 8:
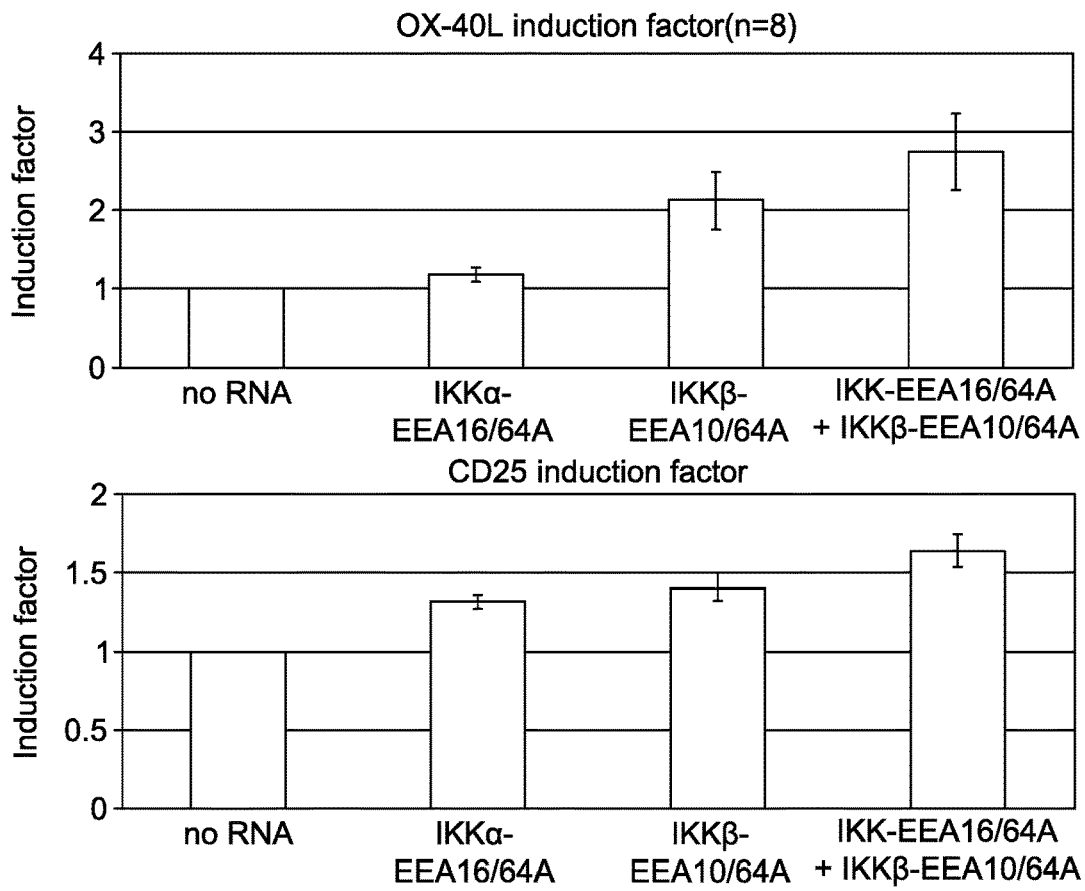
FIG. 8: Induction factor of surface markers on DCs, which were electroporated with components of the NFKB signaling pathway. DCs were produced from monocytes during a six-day culture with GM-CSF and IL-4. On Day 6, the DCs matured for 24 h after addition of a standard maturation cocktail (IL-113, IL-6, TNFa and PGE2) (mDC). Then, the DCs were electroporated without RNA, with IKKa-EE-A16-RNA (activates alternative signaling pathway), IKKß3-EEA10-RNA (activates classical signaling pathway) alone or in combination (15 ug of RNA each). These DCs were stained 24 h after EP with antibodies against OX-40L and CD25, and analyzed by FACS. The mean of 8 independent donors is provided with the standard error of the mean.

However, if RNA transfection with the activating mutants took place at the beginning of maturation (ie., in immature DCs), DCs formed that released large amounts of cytokine IL-10, which is immunosuppressive under certain conditions (FIG. 2b). Furthermore, following RNA transfection of the RNAs described above, various maturation markers on the DCs showed increased expression, including those that are thought to play a role in the communication of the DCs with other cells of the immune system (FIG. 3). In this context, particularly, the surface molecule CD70 is of interest because it is thought to play a role in the induction of long-lived memory T cells (FIG. 3, bottom). The phenotype of long-lived memory T cells was described earlier. When DCs treated in this manner were used to stimulate autologous CD8⁺ T cells repeatedly, it was observed that $NF_{\kappa}B$ activation enabled the DCs to further expand said T cells upon restimulation, wherein the T-cell phenotype of the effector memory cells was increasingly represented (FIG. 4). Another critical factor in the manufacture of immunogenic DCs is their ability to migrate, which is usually lost in IL-12-secreting DCs. Surprisingly, DCs transfected with the constitutively active $NF_{\kappa}B$ mutants were able to migrate as efficiently towards the chemokine MIP-3B, as DCs, which were electroporated with a control RNA (FIG. 5). Thus, the RNA transfection of DCs with mRNA encoding functional mutants of the NFKB signaling pathway, is a new and innovative method for the generation of immunogenic or tolerogenic DCs whose actual clinical application is looming.

In further preferred embodiments of the invention, the DC is co-transfected with mRNAs encoding CD70, optionally in combination with those encoding caTLR4 and CD40 ligand or OX40L. All molecules mentioned in this application, which are introduced into the preferably human DCs encode, preferably, molecules, which correspond to those present in humans in respect to their amino acid sequence, or are derived from them.

According to aspect (2) of the invention, the method for the ex vivo manufacture of DCs, the $NF_{\kappa}B$ signaling pathway of which has been manipulated, comprises the RNA transfection of immature or mature DCs with one or more nucleotide sequences encoding a mutant signal transducing protein of the $NF_{\kappa}B$ signaling pathway described above.

Here, preferably, RNA transfection takes place by electroporation (other methods known to the person skilled in the art, such as lipofection, etc. may also be used). A preferred embodiment of the electroporation process is the method described by Tuyaerts et al. which is particularly well suited for clinical applications (Cancer Gene Ther. 10(9) (2003), 696-706, the contents of which is expressly incorporated herein by reference). In a further preferred embodiment, the RNA transfection technology used is nucleofection (proprietary technology of Amaxa) (cf., e.g. Melhem et al., Clin. Vaccine Immunol. 15(9) (2008), 13371344). Preferred concentrations for transfection of RNA by electroporation include, in particular, about 1 µg/100 µl to about 100 µg/100 µl, more preferably 2 µg/100 µl to 50 µg/100 µl, and most preferably about 20 µg to about 40 µg/100. Besides the already mentioned electroporation, which may be effected both by a square wave pulse, as well as by an exponentially decaying pulse, mRNA transfection can be achieved by various reagents for mRNA transfection. Examples include charged and uncharged lipids by means of which DCs may be transfected with mRNA.

In the case of RNA transfection of immature DCs, the process of the invention may include further treating with a maturation stimulus. Other preferred embodiments include loading the DCs with a target antigen and/or (iii) the cryopreservation of mature DCs.

Herein, "maturation stimulus" is defined as molecules and combinations of molecules under the assistance of which immature dendritic cells become mature dendritic cells. A preferred combination of molecules herein consists of IL-1ß, IL-6, TNFα and PGE2.

In relation to the present invention, "cryopreservation" is understood to be the storage of cells by freezing at temperatures below −75° C.

The composition, pharmaceutical composition or drug according to the aspect (3) of the invention may optionally include pharmaceutically acceptable excipients and carrier compounds. For pharmaceutical use, preferably, the DCs are autologous DCs.

A "pharmaceutical composition" or "drug" includes the dendritic cells of the invention and one or more components that are administered to patients, for example, in the form of a vaccination for the treatment of cancer or HIV. Processes and means of formulating a pharmaceutical composition are known to the person skilled in the art and may be found, for example, in Ansel et al., "Pharmaceutical Dosage Forms and Drug Delivery Systems", 7th edition, Lippincott Williams & Wilkins Publishers, 1999. The pharmaceutical composition or drug may be administered to an individual in an appropriate dose. In particular, the administration can be parenteral, for example, intravenous, intraperitoneal, subcutaneous or intramuscular, or via a catheter at a site in an artery. Preparations for parenteral administration include sterile aqueous or non-aqueous solutions, suspensions and emulsions. Examples of non-aqueous solvents are propylene glycol, polyethylene glycol, vegetable oils such as olive oil, and organic ester compounds such as ethyl oleate, which are suitable for injections. Aqueous carriers include water, alcoholic-aqueous solutions, emulsions, suspensions, salt solutions and buffered media. Parenteral carriers include sodium chloride solutions, Ringer's dextrose, dextrose and sodium chloride, lactated Ringer's solution and bound oils. Intravenous carriers include, for example, liquid, nutritional and electrolyte supplements (such as those that are based on Ringer's dextrose). The pharmaceutical composition or drug may also include preservatives and other additives, such as, for example antimicrobial compounds, antioxidants or complexing agents. Furthermore, depending on the specific use intended, other agents such as interleukins, growth factors, differentiation factors, interferons, chemotactic proteins, or a non-specific immunomodulating agent may be included.

The type of dosage is determined by the treating physician according to clinical factors The person skilled in the art knows that the type of dosage depends on various factors, such as body size or weight, body surface area, age, sex or general health of the patient, but also on the particular agent to be administered, the duration and route of administration, and other drugs that may be administered in parallel. A typical dose can be, for example, in a range between 5 million and 50 million DCs per administration.

The schedule of repeated administration usually starts out with smaller intervals in the range of one to two weeks, and later on, intervals can be extended up to 6 months. In previous studies, DCs were usually injected intradermally, subcutaneously and intravenously. "Suitable excipients and carrier compounds" include components onto which the cells of the invention may be applied or introduced and, for example, protect the cells. Examples of suitable pharmaceutically acceptable excipients and carrier compounds are known to the person skilled in the art and include, for example, phosphate buffered saline, water, emulsions, such as oil/water emulsions, various types of wetting agents or detergents, sterile solutions, etc. Pharmaceutical composition or drugs comprising such carriers can be formulated by means of known conventional methods.

"Autologous" dendritic cells are understood to mean the body's own cells of a patient or cells formed from the body's own cells of a patient.

In the use of the DCs of the invention for the stimulation of autologous $CD8^+$ T cells ex vivo according to the aspect (4) of the invention, preferably, (i) $NF_K B$-activated DCs are used for passive T cell transfer and generation of a T cell clone (including subsequent TCR isolation), and (ii) $NF_K B$-repressed DCs are used for expansion of Tregs for the treatment of allergies, chronic inflammation, autoimmunity and transplant rejection.

"$CD8^+$ T cells" are characterized by the presence of the surface marker CD8 and are members of a subset of T lymphocytes, which are able to kill infected somatic cells or tumor cells.

Passive immunization or "passive T cell transfer" is understood to mean the transfer of immunological effectors or T cells generated outside of the recipient. Recipients do not have to actively develop the immune response themselves, but receive it from the outside, thus they themselves are passive. Passive immunization with T cells, which is the passive transfer of T cells, is also referred to as an adaptive T cell transfer.

In relation to the present invention, a "T cell clone" is a population of cells derived from a T cell of a patient and which may be held in culture, originating from an individual T cell. "Expansion of Treg" refers to the cultivation and proliferation of regulatory T cells, which can suppress the functions of other T cells.

"Allergies" refers to an overshooting immune response of the immune system to specific and normally harmless environmental substances (allergens).

"Autoimmunity" may be defined as an overshooting immune response of the immune system to the body's own tissues.

"TCR isolation" refers to a method for obtaining the nucleotide sequences encoding the T cell receptor (TCR) from a T cell clone. Methods for this purpose can be found in the prior art.

In the use of the DCs of the invention for the manufacture of a drug for the treatment of diseases in a patient according to aspect (5) of the invention and in the method for the treatment of cancer, infectious or autoimmune diseases in a patient, comprising administering the DCs of the invention to said patient according to aspect (7) of the invention, preferably NF$_K$B-activated DCs are used for the DC-based vaccination (especially in the absence of helper epitopes or functional helper cells, and when the use of potent adjuvants is not possible), for therapeutic vaccination against cancer or infectious diseases (including HIV) and as a preventive vaccine, and NF$_K$B-repressed DCs are used for the induction of tolerance in vivo, and for the treatment of allergies, chronic inflammation, autoimmunity and transplant rejection.

"DC-based vaccination" describes a method for administration of dendritic cells to patients, preferably by injection.

"Helper epitopes" are presented in the MHC/HLA Class II-context and can induce T-cell proliferation and the synthesis of cytokines.

"Functional helper cells" are a group of T-lymphocytes in the blood, which have a helper function. They are classified in two major subgroups based on the cytokines they release. One sub-group is involved in the cellular immune response, while the other sub-group is involved in the humoral immune response.

"Adjuvants" are excipients, which enhance the effect of a reagent or a pharmaceutical composition, in particular the immune response.

"Cancer" refers to a malignant tumor or a malignant leukemia.

"Infectious diseases" are caused by a pathogen, such as viruses, bacteria, fungi or other microorganisms.

In the present application, the "induction of tolerance in vivo" refers to the repression of an immunological response in patients, preferably in a human patient.

In the process for the expansion of T cells, including the stimulation of autologous CD8$^+$ T cells ex vivo, comprising stimulating the T cells with DCs of the invention according to aspect (6) of the invention, preferably NF$_K$B activated DCs are used for T cell expansion of T cells for the passive T cell transfer and generation of a T cell clone (e.g., for subsequent TCR isolation), and NF$_K$B-repressed DCs are used for expansion of Tregs for the treatment of allergies, chronic inflammation, autoimmunity and transplant rejection.

A desired improved T cell proliferation, and thus an improved medicinal effect may also be achieved by the co-administration or simultaneous expression in the DC via transfected mRNA(s) of antibodies, preferably against CTLA-4, PD-L1, PD-L2, PD1, or by an agonistic anti-GITR antibody (cf., e.g., Leach et al., Science 271 (1996), 1734-1736; Quezada et al., J. Clin. Invest., 116(7) (2006), 19351945).

A further embodiment relates to a method for the treatment of diseases in a patient, comprising administering the DCs of the invention to said patient, wherein preferably (i) NF$_K$B-activated DCs are used for DC-based vaccination (especially in the absence of helper epitopes or functional helper cells, and when the use of potent adjuvants is not possible), for the therapeutic vaccination against cancer or infectious diseases (including HIV) and/or as a preventive vaccine, and (ii) NFKB-repressed DCs are used for the induction of tolerance in vivo, and for the treatment of allergies, chronic inflammation, autoimmunity and transplant rejection.

Potential therapeutic applications of dendritic cells will be discussed below. A possible strategy for the treatment of a cancer patient involves obtaining monocytes from the blood of said patient, the differentiation of these monocytes into dendritic cells (DCs) by means of GM-CSF and IL-4, or similarly acting cytokines; the maturation of said DCs by IL-1beta, IL-6, TNF, and PGE2, or similarly acting maturation stimulators; the electroporation of said DCs with mRNA the sequence of which encodes one or both of the NFkappaB-activating mutants of IKK-alpha and IKK-beta; the loading of said DCs with one or more tumor-associated antigen(s) by either co-electroporation of an mRNA, the sequence of which encodes for it(them), or by exogenous loading of said DCs with one or more synthetic peptide(s) which can bind to HLA molecules of said DCs; the cryopreservation of said DCs in suitable portions; quality control of said DCs by determination of IL-12p70 secretion; the intravenous or intra- or subdermal injection of said DCs into said patient in multiple staggered doses.

According to the invention, in the manufacture of the DCs the direct recovery of DCs from fresh or cryopreserved patient material is contemplated, including but not limited to blood or blood cells or other tissue of the patient, by magnetic or fluorescence activated cell sorting or the differentiation of the DCs from bone marrow stem cells, which were purified, for example, via the stem cell marker CD34. For the differentiation of the monocytes and the stem cells to DCs, besides GM-CSF and IL-4, other substances may be used including, but not limited to: Flt3 ligand, IL-15, IFN-alpha, TNF.

Inter alia, autologous and allogeneic tumor material, and mRNA derived thereof and amplified, and also enzymatically produced mRNA encoding tumor antigens or parts thereof, may be used as antigen sources for antigen loading. HLA-binding peptides derived from tumor antigens may be loaded directly on the HLA molecules of the DCs. Genetically engineered tumor proteins or recombinant proteins combining tumor antigens, or parts thereof, with receptor agonists, which mediate the entry into the DCs, may also be used. These methods of antigen loading may be applied in the immature and/or mature stage of the DCs.

A possible strategy for the manufacture of antigen-specific cytotoxic T cells for the autologous or allogeneic adaptive T cell therapy involves the manufacture of NFkappaB-activated DCs, as described in the example, the isolation of T cells from fresh or cryopreserved patient material, including but not limited to blood or blood cells or other tissue of the patient, furthermore the antigen-specific proliferation of these T cells by repeated incubation with said NF$_K$B-activated DCs, which are loaded with the corresponding antigen, the cryopreservation of the T cells in appropriate portions, quality control of the T cells by determining their antigen-specific lytic activity and their ability to antigen-specific cytokine secretion, the intravenous, intratumoral, intraperitoneal, or other injection of the T cells into said patient in one or more staggered doses. Unless otherwise defined, the terms used herein have the same meaning as in the prior art. The invention is further illustrated by the following examples, they do not limit the scope of the application by any means.

Sequence Listing, Free Text:

| SEQ ID NO: | Description |
|---|---|
| 1 | Wild-type IKKα protein |
| 2 | IKKα-EEA16/64A protein (AS 1-24 TAG) |
| 3 | IKKα-EEA16/64A nucleotide sequence |

-continued

| SEQ ID NO: | Description |
|---|---|
| 4 | Wild-type IKKß protein |
| 5 | IKKß-EEA10/64 protein (AS 1-17 TAG) |
| 6 | IKKß-EEA10/64 nucleotide sequence |
| 7 | IKKα-K44MA16/64A protein (AS 1-23 TAG) |
| 8 | IKKα-K44MA16/64A nucleotide sequence |
| 9 | IKKß-K44MA10/64 protein (AS 1-23 TAG) |
| 10 | IKKß-K44MA10/64 nucleotide sequence |

EXAMPLES

Materials and Methods

Electroporation of DCs: Mature or immature DCs were adjusted at about 40-60×10$^6$ cells/ml using OptiMEM (minimum volume for a 4 mm electroporation cell: 100 µl) and pipetted into the prepared cells. In the meantime, the cell was charged with RNA encoding IKKß-EEA10, IKKα-EEA16. Electroporation was performed with the program square-wave pulse at 500 V for 1 ms (4 mm cell). Immediately after electroporation, the DCs were transferred into previously prepared DC medium (incl. IL-4 and GM-CSF) and incubated in an incubator for the following experiments. When immaturely transfected DCs were matured after electroporation, maturing cocktail IL1-ß, IL-6, TNFα and PGE$_2$) was added to the DC medium.

A: Sequences of Constitutively Active IKKα and IKKß Mutants

1. IKKα-EEA16/64A sequence (SEO ID NO:2): Comparison IKKα-EEA16/64A amino acid sequence (SEQ ID NO:2) with amino acid sequence of wild-type IKKα (SEQ ID NO:1): EE mutations (at pos. 200 und 204 of SEQ ID NO:2) cause constitutive activity of IKKα, A16 mutations (at pos. 685, 686, 689, 693, 694, 700, 703, 704, 710, 711, 717, 719, 723, 729, 730, 745 und 746 of SEQ ID NO: 2) remove destabilizing serines und threonines, leading to a largely increased stability of the protein. The corresponding nucleotide sequence is shown in SEQ ID NO:3.

2. IKKß-EEA10/64 sequence (SEQ ID NO:5): Comparison IKKß-EEA16/64A amino acid sequence (SEQ ID NO:5) with amino acid sequence of wild-type IKKß (SEQ ID NO:4): EE mutations (at pos. 231 und 235 of SEQ ID NO:5) cause constitutive activity of IKKß, A10 mutations (at pos. 724, 726, 729, 733, 736, 743, 746, 749, 751, und 759 of SEQ ID NO:2) remove destabilizing serines, leading to a largely increased stability of the protein. The corresponding nucleotide sequence is shown in SEQ ID NO:6.

B: Sequences of Inhibitory IKKα and IKKß Mutants

3. IKKα-K44MA16/64A sequence (SEQ ID NO:7): Comparison IKKα-K44MA16/64A amino acid sequence (SEQ ID NO:7) with wild-type IKKα amino acid sequence. (SEQ ID NO: 1). The kinase activity is inhibited by an exchange of the as lysine (Lys44; pos. 67 in SEQ ID NO:7) at the ATP binding site by methionine. By dimerization, this mutant has a dominant negative effect. A16 mutations (pos. 684, 685, 688, 692, 693, 699, 702, 703, 709, 710, 716, 718, 722, 728, 729, 744, and 745 of SEQ ID NO:7) remove destabilizing serines and threonines, resulting in a largely increased stability of the protein. The corresponding nucleotide sequence is shown in SEQ ID NO:8.

4. IKKß-K44MA16/64A sequence (SEQ ID NO:9): Comparison IKKß-K44MA16/64A amino acid sequence (SEQ ID NO:9) with wild-type IKKß amino acid sequence. (SEQ ID NO:4). The kinase activity is inhibited by an exchange of the as lysine (Lys44; pos. 67 in SEQ ID NO:9) at the ATP binding site by methionine. By dimerization, this mutant has a dominant negative effect. A10 mutations (pos. 693, 695, 698, 702, 705, 712, 715, 718, 720, and 728 of SEQ ID NO:9) remove destabilizing serines, resulting in a largely increased stability of the protein. The corresponding nucleotide sequence is shown in SEQ ID NO:10.

Example 1: Secretion of IL-12p70 and IL-10 by IKKß3-EEA10-RNA-electroporated dendritic cells.

Dendritic cells, immature (iDC) or mature (mDC) without RNA, were electroporated with a control RNA or IKKß3-EEA10-RNA (SEQ ID NO:6). Immediately after electroporation, half of the immaturely electroporated cells were matured (iDCm). Twenty-four hours after electroporation, the cytokine concentrations (IL-12p70 and IL-10) in the supernatants were determined in a cytometric bead array (CBA). FIGS. 2(*a*) and (*b*), respectively, show data of one representative of four independent experiments.

Example 2: Expression of surface markers on dendritic cells transfected with the NF$_K$B signaling pathway component IKKß3-EEA10. Immature (iDC) and mature (mDC) dendritic cells were electroporated with RNA encoding IKKß-EEA10 (SEQ ID NO:6). After electroporation, half of the immaturely electroporated cells were treated with maturation cocktail (iDCm). As control conditions, DCs were electroporated without RNA or with irrelevant RNA (control RNA). After electroporation, the DCs were cultured in DC medium for 24 h, harvested and stained with a PE-labeled antibody against CD40, CD80 and CD70. The PE label identifies the coupling of the pigment phycoerythrin and an antibody. The mean fluorescence intensity (MFI) of the electroporated dendritic cells was determined by flow cytometry. The values given in FIG. 3 show the specific MFI, which was calculated from the measured relative fluorescence minus the measured fluorescence of the isotype antibody. The data represent one representative of four independent experiments.

Example 3: Tetramer staining of the stimulation of autologous T cells with dendritic cells electroporated with RNA of NF$_K$B signaling pathway components. Mature dendritic cells were electroporated with control RNA, IKKß-EEA10-RNA (SEQ ID NO:6) and IKKα-EE-RNA, or with a combination of IKKß-EEA10 and IKKα-EE-RNA. A portion of the cells was co-electroporated with RNA encoding the tumor marker MelanA, (+ MelanA RNA). Three hours after electroporation, one half of the condition series without MelanA was loaded with MelanA/A2-peptide for 1 h (+peptide loading). Four hours after electroporation, autologous CD8$^+$ T cells were stimulated with said dendritic cells in the ratio 10:1. After one week, the number of antigen-specific T cells was analyzed and their phenotype determined by CCR7 and CD45RA staining. Said T cells were analyzed following a priming FIG. 4*a* and after a restimulation FIG. 4*b*.

The figures show data from one donor.

Example 4: Migration of mature dendritic cells 24 h after RNA transfection with NF$_K$B signaling pathway components.

Mature DCs were electroporated with RNA encoding GFP, IKKß3-EEA10 (SEQ ID NO:6) and IKKα-EE, alone and in combination. After electroporation, said DCs were cultured for 24 h and then tested for their ability to migrate for 2 h in a transwell assay. The results are shown in FIG. 5 (condition without chemokine (=neg); chemokine in the insert (=anti); chemokine in the depression (=to)). The data shown represent mean values with the standard deviation of three independent experiments.

Example 5: Improvement of DCs by RNA transfection with NF$_K$B mutants.

Stimulation of DCs with components of the NF$_K$B signaling pathway, IKKß3-EE-A10 and IKKα-EE-A16 (SEQ ID NO:3): the following constructs were used: IKK↓-EE-A10 stimulates the classical NF$_K$B signaling pathway leading to the activation and maturation of the DCs, and IKKα-EE-A16 is an activator of the alternative NFKB signaling pathway.

Figure 9:
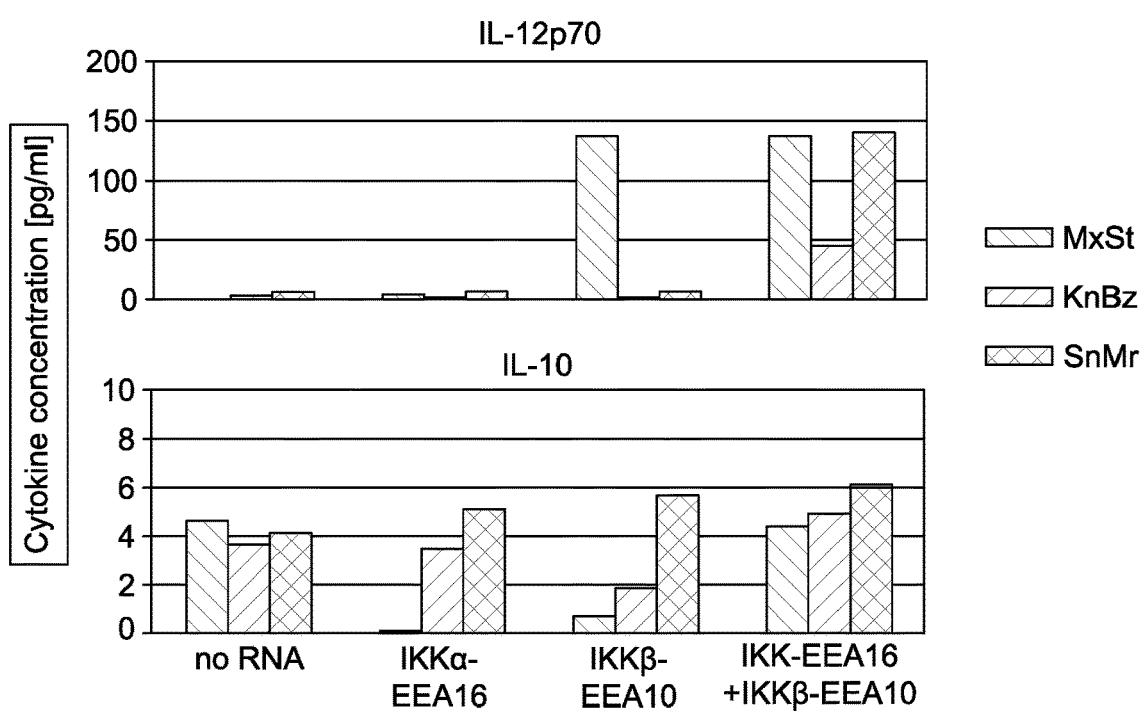
FIG. 9: Secretion of cytokines IL-12p70 and IL-10 by DCs, which were electroporated with components of the NFKB signaling pathway. DCs were produced from monocytes during a six-day culture with GM-CSF and IL-4. On Day 6, the DCs matured for 24 h after addition of a standard maturation cocktail (IL-113, IL-6, TNFa and PGE2) (mDC). Then, the DCs were electroporated without RNA, with IKKa-EE-A16-RNA (activates alternative signaling pathway), IKKß3-EEA10-RNA (activates classical signaling pathway) alone or in combination (15 ug of RNA each). 24 h after EP, the supernatants were collected and analyzed by an "inflammation cytometric bead array". The data from 3 independent donors are shown.
Figure 10:
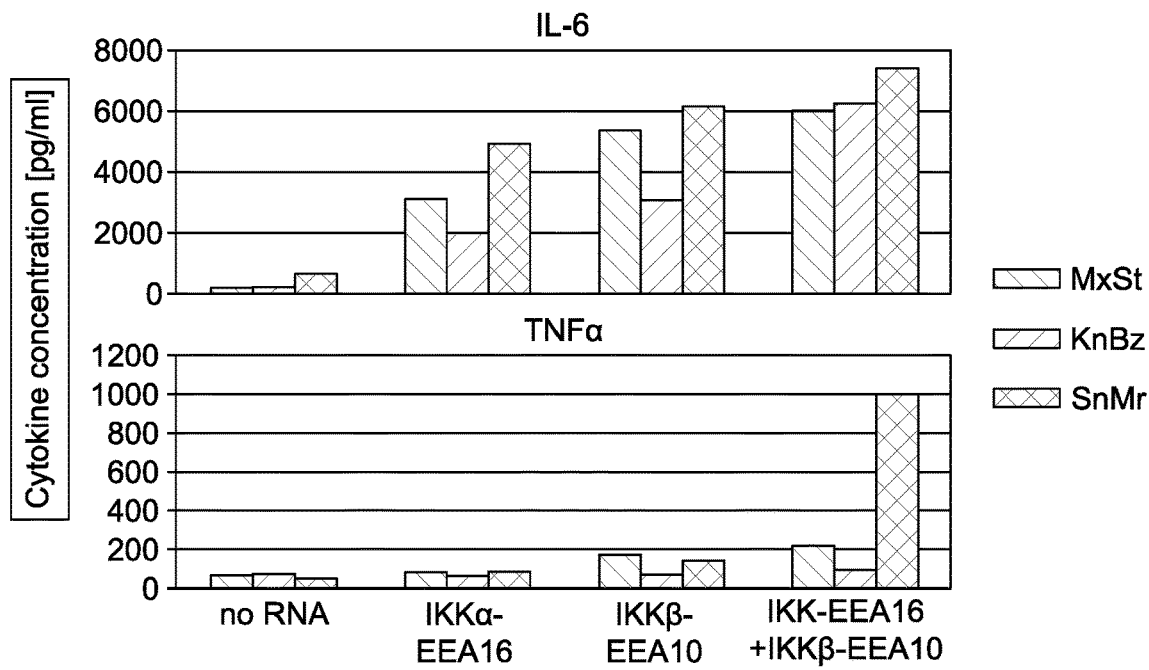
FIG. 10: Secretion of cytokines IL-6 and TNFa by DCs, which were electroporated with components of the NFKB signaling pathway. DCs were produced from monocytes during a six-day culture with GM-CSF and IL-4. On Day 6, the DCs matured for 24 h after addition of a standard maturation cocktail (IL-1B, IL-6, TNFa and PGE2) (mDC). Then, the DCs were electroporated without RNA, with IKKa-EE-A16-RNA (activates alternative signaling pathway), IKKß-EEA10-RNA (activates classical signaling pathway) alone or in combination (15 ug of RNA each). 24 h after EP, the supernatants were collected and analyzed by an "inflammation cytometric bead array". The data from 3 independent donors are shown.
Figure 11:
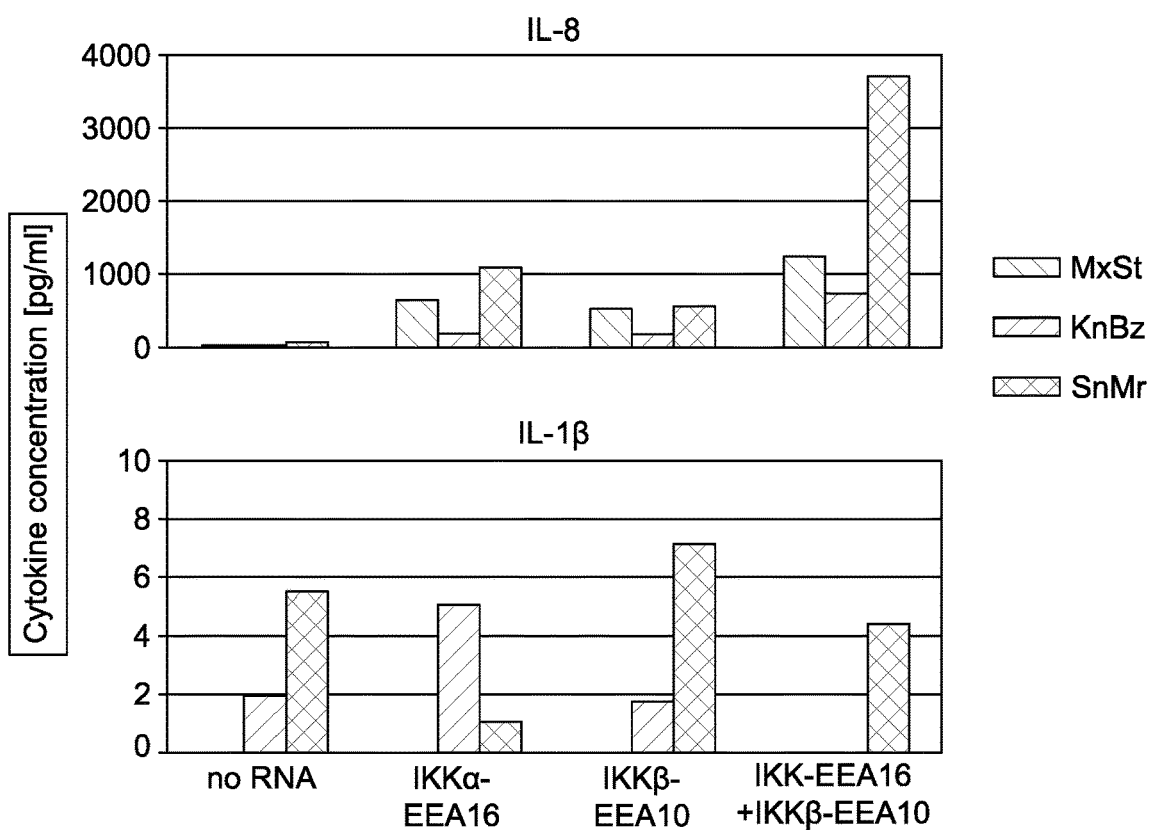
FIG. 11: Secretion of cytokines IL-8 and IL-1ß by DCs, which were electroporated with components of the NFKB signaling pathway. DCs were produced from monocytes during a six day culture with GM-CSF and IL-4. On Day 6, the DCs matured for 24 h after addition of a standard maturation cocktail (IL-1ß, IL-6, TNFa and PGE2) (mDC).

The effects of electroporation with IKKß3-EE-A10 were mainly an up-regulation of surface markers (CD25, CD40, CD70, CD80, CD83 and OX-40L, FIGS. 6-8) and an up-regulation of the cytokine secretion, and in particular of IL12p70, while IL-10 was secreted in very small amounts (FIG. 9). Other secreted cytokines were: IL-6, TNFα (FIG. 12), IL-8 and IL-1B (FIG. 11). These effects were enhanced as RNA of the activators of the classical and the alternative NF$_K$B signaling pathway (IKK___-EE-A10 and IKKα-EE-A16) were co-electroporated (FIGS. 6-11). Electroporation of IKKα-EE-A16 RNA alone had comparable effects as slightly smaller amounts of the secreted cytokines and the expression of surface markers (FIG. 6-11). Particularly after the third stimulation, electroporated mDCs showed a much greater stimulatory capacity in regards to autologous T cells (FIG. 12). DCs that were electroporated with only a single activator (IKKα-EE-A16 or IKKß-EE-A10) had similar stimulatory capacities (up to three times compared to the control condition Mela), while the DCs, which were electroporated with both activators had the highest capacity for stimulation of specific T cells (seven-fold expansion of specific T cells).

Dose dependence experiments were performed to determine the best amount of RNA that should be used during the RNA transfection of DCs. Mature DCs were electroporated with increasing RNA concentrations. Increasing expression patterns of surface markers (CD25, CD40, CD70 and OX-40L) were obtained depending on the concentration of the transfected RNA (FIG. 13). But, nevertheless, the state of electroporation with both activators IKKß-EE-A10 and IKKα-EE-A16 (15 µg each) led to an increased expression of all markers, in particular CD70, as compared to 30 µg of RNA from one activator alone.

In cytokine secretion, a dose-dependent up-regulation was obtained, in particular of IL12p70, whereas IL-10 was secreted in a very low amount (FIG. 14). Moreover, the secretion of IL-6, IL-8 and TNF was dose-dependent with a similar pattern (data not shown). Here, the amount of secreted cytokines was not higher when RNA of activators of the classical and the alternative NF$_K$B signaling pathway (IKKß-EE-A10 and IKKα-EE-A16) were co-electroporated (compare 30 µg of each RNA with a combination of 15 µg of RNA of both activators).

Example 6: NF$_K$B activity in transfected 293T cells: 293T cells were electroporated with activators of both NF$_K$B signaling pathways and co-electroporated with a vector encoding luciferase under the control of an NF$_K$B promoter. In all cases (IKKα-EE-A16 and IKKß3-EE-A10 alone or in combination), luciferase activity was measured 24 h after electroporation (FIG. 15). Again, the case of RNA transfection with both activators showed the biggest effect.

This assay was also performed with DCs, but produced no results (data not shown).

IKKß3-K44M-A10 and IKKα-K44M-A16: Using an inhibitor of the classical (IKKß-K44M-A10) and the alternative NF$_K$B signaling pathway (IKKα-K44M-A16), a luciferase assay was performed with 293T cells which were electroporated with IKKα-K44M-A16 or IKKß-K44M-A10 RNA alone or in combination, and were co-electroporated with luciferase vectors comprising an NF$_K$B promoter. NF$_K$B signaling pathways of transfected 293T cells were activated overnight with soluble CD40L. Luciferase activity was measured 24 h after electroporation. Both inhibitors were clearly able to reduce luciferase activity in comparison with the positive control, which has been transfected only with luciferase vector and activated with soluble CD40L (FIG. 15).

EXAMPLE 7: Secretion of IL-12p70 in mature dendritic cells that have been transfected with RNA encoding constitutively active TKK mutants.

On Day 6, dendritic cells derived from monocytes were matured for 24 h using the standard maturation cocktail (IL-1ß, IL-6, TNFα and PGE2) and then electroporated. Said cells were transfected without RNA, with RNA encoding the constitutively active mutants IKKαFEA16 and IKKßEEA10, and with a combination of both RNAs (see FIG. 16).

Subsequently, the concentration of IL-12p70 in the medium was measured 4 h, 24 h and 48 h after electroporation. Here, the production of IL12p70 was observed over a period of 2 days. The use of both mutants led to the highest IL-12p70 production. One representative experiment of three is shown.

Example 8: Migration of mature dendritic cells that have been transfected with RNA encoding constitutively active IKK mutants. On Day 6, dendritic cells derived from monocytes were matured for 24 h using the standard maturation cocktail (IL-1ß, IL-6, TNFα and PGE2) and then electroporated. Said cells were transfected with 5 µg/100 µl of RNA encoding Melan A, and, with 15 µg/100 µl of RNA, encoding constitutively active mutants of IKKα and IKKß, and encoding a combination of both RNAs (see FIG. 17). Then, the ability of the transfected cells to migrate to the chemokine CCL19 was studied. The results are shown in FIG. 17 (condition without chemokine (=neg); chemokine in the insert (=anti); chemokine in the depression (=zu)). Means with standard errors from 4 independent experiments are shown.

The invention claimed is:

1. A method for treating infectious diseases or cancer in a patient comprising administering a composition comprising dendritic cells to the patient, wherein the dendritic cells comprise an NFκB signaling pathway that has been manipulated by RNA transfection with one or more nucleotide sequences encoding at least one mutant signal transducing protein of the NFκB signaling pathway, wherein the mutant signal transducing protein of the NFκB signaling pathway is a constitutively active IKKα mutant comprising the amino acid residues of SEQ ID NO:2 or IKKβ mutant comprising the amino acid residues of SEQ ID NO:5.

2. The method of claim 1, wherein the dendritic cells are NFκB-activated dendritic cells.

3. The method of claim 2, wherein the NFκB-activated dendritic cells produce IL-12p70.

4. The method of claim 2, wherein the NFκB-activated dendritic cells produce IL-10.

5. The method of claim 2, wherein the NFκB-activated dendritic cells are administered as a vaccine against a cancer or an infectious disease.

6. The method of claim 5, wherein the infectious disease is HIV.

7. The method of claim 5, wherein the NFκB-activated dendritic cells are administered as a vaccine against a cancer.

8. The method of claim 2, wherein the NFκB-activated dendritic cells are used for the treatment of cancer.

9. The method of claim 1, wherein the composition further comprises pharmaceutically acceptable excipients and carrier compounds.

10. The method of claim 1, wherein the dendritic cells are autologous dendritic cells.

11. The method of claim 1, wherein the dendritic cells are mature dendritic cells.

12. The method of claim 1, wherein the composition further comprises one or more target antigens.

* * * * *

SEQUENCE LISTING

```
Sequence total quantity: 10
SEQ ID NO: 1          moltype = AA  length = 745
FEATURE               Location/Qualifiers
source                1..745
                      mol_type = protein
                      organism = Homo sapiens
SEQUENCE: 1
MERPPGLRPG AGGPWEMRER LGTGGFGNVC LYQHRELDLK IAIKSCRLEL STKNRERWCH   60
EIQIMKKLNH ANVVKACDVP EELNILIHDV PLLAMEYCSG GDLRKLLNKP ENCCGLKESQ  120
ILSLLSDIGS GIRYLHENKI IHRDLKPENI VLQDVGGKII HKIIDLGYAK DVDQGSLCTS  180
```

```
FVGTLQYLAP  ELFENKPYTA  TVDYWSFGTM  VFECIAGYRP  PLHHQPFTW   HEKIKKKDPK   240
CIFACEEMSG  EVRFSSHLPQ  PNSLCSLIVE  PMENWLQLML  NWDPQQRGGP  VDLTLKQPRC   300
FVLMDHILNL  KIVHILNMTS  AKIISFLLPP  DESLHSLQSR  IERETGINTG  SQELLSETGI   360
SLDPRKPASQ  CVLDGVRGCD  SYMVYLFDKS  KTVYEGPFAS  RSLSDCVNYI  VQDSKIQLPI   420
IQLRKVWAEA  VHYVSGLKED  YSRLFQGQRA  AMLSLLRYNA  NLTKMKNTLI  SASQQLKAKL   480
EFFHKSIQLD  LERYSEQMTY  GISSEKMLKA  WKEMEEKAIH  YAEVGVIGYL  EDQIMSLHAE   540
IMELQKSPYG  RRQGDLMESL  EQRAIDLYKQ  LKHRPSDHSY  SDSTEMVKII  VHTVQSQDRV   600
LKELFGHLSK  LLGCKQKIID  LLPKVEVALS  NIKEADNTVM  FMQGKRQKEI  WHLLKIACTQ   660
SSARSLVGSS  LEGAVTPQTS  AWLPPTSAEH  DHSLSCVVTP  QDGETSAQMI  EENLNCLGHL   720
STIIHEANEE  QGNSMMNLDW  SWLTE                                           745

SEQ ID NO: 2           moltype = AA   length = 769
FEATURE                Location/Qualifiers
REGION                 1..769
                       note = IKKalpha Contistitutive Active Mutant
source                 1..769
                       mol_type = protein
                       organism = synthetic construct
SEQUENCE: 2
HHHHHGDYKD  DDDKGDIEGR  GHMTMERPPG  LRPGAGGPWE  MRERLGTGGF  GNVCLYQHRE    60
LDLKIAIKSC  RLELSTKNRE  RWCHEIQIMK  KLNHANVVKA  CDVPEELNIL  IHDVPLLAME   120
YCSGGDLRKL  LNKPENCCGL  KESQILSLLS  DIGSGIRYLH  ENKIIHRDLK  PENIVLQDVG   180
GKIIHKIIDL  GYAKDVDQGE  LCTEFVGTLQ  YLAPELFENK  PYTATVDYWS  FGTMVFECIA   240
GYRPFLHHLQ  PFTWHEKIKK  KDPKCIFACE  EMSGEVRFSS  HLPQPNSLCS  LIVEPMENWL   300
QLMLNWDPQQ  RGGPVDLTLK  QPRCFVLMDH  ILNLKIVHIL  NMTSAKIISF  LLPPDESLHS   360
LQSRIERETG  INTGSQELLS  ETGISLDPRK  PASQCVLDGV  RGCDSYMVYL  FDKSKTVYEG   420
PFASRSLSDC  VNYIVQDSKI  QLPIIQLRKA  WAEAVHYVSG  LKEDYSRLFQ  GQRAAMLSLL   480
RYNANLTKMK  NTLISASQQL  KAKLEFFHKS  IQLDLERYSE  QMTYGISSEK  MLKAWKEMEE   540
KAIHYAEVGV  IGYLEDQIMS  LHAEIMELQK  SPYGRRQGDL  MESLEQRAID  LYKQLKHRPS   600
DHSYSDSTEM  VKIIVHTVQS  QDRVLKELFG  HLSKLLGCKQ  KIIDLLPKVE  VALSNIKEAD   660
NTVMFMQGKR  QKEIWHLLKI  ACTQAAARAL  VGAALEGAVA  PQAAAWLPPA  AAEHDHALAC   720
VVAPQDGEAA  AQMIEENLNC  LGHLAAIIHE  ANEEQGNSMM  NLDWSWLTE                769

SEQ ID NO: 3           moltype = DNA   length = 2238
FEATURE                Location/Qualifiers
misc_feature           1..2238
                       note = IKKalpha Constitutive Active Mutant
source                 1..2238
                       mol_type = other DNA
                       organism = synthetic construct
SEQUENCE: 3
atggagcggc  cccgggggct  gcggccgggc  gcgggcggc   cctgggagat  gcgggagcgg    60
ctgggcaccg  gcggcttcgg  gaacgtctgt  ctgtaccagc  atcgggaact  tgatctcaaa   120
atagcaatta  agtcttgtcg  cctagagcta  agtaccaaaa  acagagaacg  atggtgccat   180
gaaatccaga  ttatgaagaa  gttgaaccat  gccaatgttg  taaaggcctg  tgatgttcct   240
gaagaattga  atattttgat  tcatgatgtg  cctcttctag  caatgaaata  ctgttctgga   300
ggagatctcc  gaaagctgct  caacaaacca  gaaaattgtt  gtggacttaa  agaaagccag   360
atactttctt  tactaagtga  tatagggtct  gggattcgat  atttgcatga  aaacaaaatt   420
atacatcgag  atctaaaacc  tgaaaacata  gttcttcagg  atgttggtgg  aaagataata   480
cataaaataa  ttgatctggg  atatgccaaa  gatgttgatc  aaggagagct  gtgtacagag   540
tttgtgggaa  cactgcagta  tctgccccca  gagctctttg  agaataagcc  ttacacagct   600
actgttgatt  attggagctt  tgggaccatg  gtatttgaat  gtattgctgg  atataggcct   660
tttttgcatc  atctgcagcc  atttacctgg  catgagaaga  ttaagaagaa  ggatccaaag   720
tgtatatttg  catgtgaaga  gatgtcagga  gaagttcggt  ttagtagcca  tttacctcaa   780
ccaaatgcc   tttgtagttt  aatagtagaa  cccatgaaca  actggctaca  gttgatgttg   840
aattgggacc  ctcagcagag  aggaggacct  gttgacctta  cttttgaagca gccaagatgt   900
tttgtattaa  tggatcacat  tttgaatttg  aagatagtac  acatcctaaa  tatgacttct   960
gcaaagataa  tttctttct   gttaccacct  gatgaaagtc  ttcattcatt  acagtctcgt  1020
attgagcgtg  aaactggaat  aaatactggt  tctcaagaac  ttcttttcaga gacaggaatt  1080
tctctggatc  ctcggaaacc  agcctctcaa  tgtgttctag  atggagttag  aggctgtgat  1140
agctatatgg  tttatttgtt  tgataaaagt  aaaactgtat  atgaagggcc  atttgcttcc  1200
agaagtttat  ctgattgtgt  aaattatatt  gtacaggaca  gcaaaataca  gcttccaatt  1260
atacagctgc  gtaaagcgtg  ggctgaagca  gtgcactatg  tgtctggact  aaaagaagac  1320
tatagcaggc  tcttttcaggg acaaagggca  gcaatgttaa  gtcttcttag  atatatagtt  1380
aacttaacaa  aaatgaagaa  cactttgatc  tcagcatcac  aacaactgaa  agctaaattg  1440
gagttttttc  acaaaagcat  tcagcttgac  ttggagagat  acagcgagca  gatgacgtat  1500
gggatatctt  cagaaaaaat  gctaaaagca  tggaaagaaa  tggaagaaaa  ggccatccac  1560
tatgctgagg  ttggtgtcat  tggataccttg  gaggatcaga  ttatgtcttt  gcatgctgaa  1620
atcatggaac  tacagaaagc  ccctatgga   agacgtcagg  gagacttgat  ggaatctctg  1680
gaacagcgtg  ccattgatct  atataagcag  ttaaaacaca  gaccttcaga  tcactcctac  1740
agtgacagca  cagagatggt  gaaaatcatt  gtgcacactg  tgcagagtca  ggaccgtgtg  1800
ctcaaggagc  tgtttggtca  tttgagcaag  ttgttgggct  gtaagcagaa  gattattgat  1860
ctactcccta  aggtggaagt  ggccctcagt  aatatcaaag  aagctgacaa  tactgtcatg  1920
ttcatgcagg  gaaaaaggca  gaaagaaatc  tggcatctta  aaattgc     tgtacacag   1980
gccgctgccc  gcgcccttgt  gggagccgct  ctgaaggtg   cagtggcccc  acaggccgcc  2040
gcatggctgc  cccctgctgc  cgcagaacac  gatcacgctc  tggcctgtgt  ggtggctcct  2100
caagatgggg  aggctgccgc  acaaatgatc  gaagaaaatt  tgaactgcct  tggccacttg  2160
gccgctatta  ttcacgaggc  aaatgaggaa  cagggcaata  gtatgatgaa  tcttgattgg  2220
agttggttga  cagaatga                                                    2238
```

```
SEQ ID NO: 4              moltype = AA  length = 756
FEATURE                   Location/Qualifiers
source                    1..756
                          mol_type = protein
                          organism = Homo sapiens
SEQUENCE: 4
MSWSPSLTTQ TCGAWEMKER LGTGGFGNVI RWHNQETGEQ IAIKQCRQEL SPRNRERWCL    60
EIQIMRRLTH PNVVAARDVP EGMQNLAPND LPLLAMEYCQ GGDLRKYLNQ FENCCGLREG   120
AILTLLSDIA SALRYLHENR IIHRDLKPEN IVLQQGEQRL IHKIIDLGYA KELDQGSLCT   180
SFVGTLQYLA PELLEQQKYT VTVDYWSFGT LAFECITGFR PFLPNWQPVQ WHSKVRQKSE   240
VDIVVSEDLN GTVKFSSSLP YPNNLNSVLA ERLEKWLQLM LMWHPRQRGT DPTYGPNGCF   300
KALDDILNLK LVHILNMVTG TIHTYPVTED ESLQSLKARI QQDTGIPEED QELLQEAGLA   360
LIPDKPATQC ISDGKLNEGH TLDMDLVFLF DNSKITYETQ ISPRPQPESV SCILQEPKRN   420
LAFFQLRKVW GQVWHSIQTL KEDCNRLQQG QRAAMMNLLR NNSCLSKMKN SMASMSQQLK   480
AKLDFFKTSI QIDLEKYSEQ TEFGITSDKL LLAWREMEQA VELCGRENEV KLLVERMMAL   540
QTDIVDLQRS PMGRKQGGTL DDLEEQAREL YRRLREKPRD QRTEGDSQEM VRLLLQAIQS   600
FEKKVRVIYT QLSKTVVCKQ KALELLPKVE EVVSLMNEDE KTVVRLQEKR QKELWNLLKI   660
ACSKVRGPVS GSPDSMNASR LSQPGQLMSQ PSTASNSLPE PAKKSEELVA EAHNLCTLLE   720
NAIQDTVREQ DQSFTALDWS WLQTEEEEHS CLEQAS                             756

SEQ ID NO: 5              moltype = AA  length = 773
FEATURE                   Location/Qualifiers
REGION                    1..773
                          note = IKKbeta constitutive active mutant
source                    1..773
                          mol_type = protein
                          organism = synthetic construct
SEQUENCE: 5
MDYKDDDDKG DIEGRGHMSW SPSLTTQTCG AWEMKERLGT GGFGNVIRWH NQETGEQIAI    60
KQCRQELSPR NRERWCLEIQ IMRRLTHPNV VAARDVPEGM QNLAPNDLPL LAMEYCQGGD   120
LRKYLNQFEN CCGLREGAIL TLLSDIASAL RYLHENRIIH RDLKPENIVL QQGEQRLIHK   180
IIDLGYAKEL DQGELCTEFV GTLQYLAPEL LEQQKYTVTV DYWSFGTLAF ECITGFRPFL   240
PNWQPVQWHS KVRQKSEVDI VVSEDLNGTV KFSSSLPYPN NLNSVLAERL EKWLQLMLMW   300
HPRQRGTDPT YGPNGCFKAL DDILNLKLVH ILNMVTGTIH TYPVTEDESL QSLKARIQQD   360
TGIPEEDQEL LQEAGLALIP DKPATQCISD GKLNEGHTLD MDLVFLFDNS KITYETQISP   420
RPQPESVSCI LQEPKRNLAF FQLRKVWGQV WHSIQTLKED CNRLQQGQRA AMMNLLRNNS   480
CLSKMKNSMA SMSQQLKAKL DFFKTSIQID LEKYSEQTEF GITSDKLLLA WREMEQAVEL   540
CGRENEVKLL VERMMALQTD IVDLQRSPMG RKQGGTLDDL EEQARELYRR LREKPRDQRT   600
EGDSQEMVRL LLQAIQSFEK KVRVIYTQLS KTVVCKQKAL ELLPKVEEVV SLMNEDEKTV   660
VRLQEKRQKE LWNLLKIACS KVRGPVAGAP DAMNAARLAQ PGQLMAQPAT AANALPEPAK   720
KAEELVAEAH NLCTLLENAI QDTVREQDQS FTALDWSWLQ TEEEEHSCLE QAS           773

SEQ ID NO: 6              moltype = DNA  length = 2319
FEATURE                   Location/Qualifiers
misc_feature              1..2319
                          note = IKKbeta constitutive active mutant
source                    1..2319
                          mol_type = other DNA
                          organism = synthetic construct
SEQUENCE: 6
atggactaca aggacgacga tgacaaaggt gacatcgaag gtagaggtca tatgagctgg    60
tcaccttccc tgacaacgca gacatgcggg gcctgggaaa tgaaagagcg ccttgggaca   120
gggggatttg gaaatgtcat ccgatggcac aatcaggaaa caggtgagca gattgccatc   180
aagcagtgcc ggcaggagct cagccccgg aaccagtggt ggtgcct ggagatgtccc ggagggatg   240
atcatgagaa ggctgaccca ccccaatgtg gtggctgccc gagatgtccc tgagggggatg   300
cagaacttgg cgcccaatga cctgcccctg ctggccatgg agtactgcca aggaggagat   360
ctccggaagt acctgaacca gtttgagaac tgctgtggtc tgcgggaagg tgccatcctc   420
accttgctga gtgacattgc ctctgcgctt agatacctcat atgaaaacag aatcatccat   480
cgggatctaa agccagaaaa catcgtcctg cagcaaggag aacagaggtt aatacacaaa   540
attattgacc taggatatgc caaggagctg gatcagggcg agctttgcac agagttcgtg   600
gggaccctgc agtacctggc cccagagcta ctggagcagc agaagtacac agtgaccgtc   660
gactactgga gcttcggcac cctggccttt gagtgcatca cgggcttccg gccccttcctc   720
cccaactggc agcccgtgca gtggcattca aaagtgcgtc agaagagtga ggtggacatt   780
gttgttagcg aagacttgaa tggaacggtg aagttttcaa gctctttacc ctaccccaat   840
aatcttaaca gtgtcctggc tgagcgactg gagaagtggc tgcaactgat gctgatgtgg   900
cacccccgac agagggcac ggatcccacg tatgggccca atggctgctt caaggccctg   960
gatgacatct taaacttaaa gctggttcat atcttgaaca tggtcacggg caccatccat  1020
acctaccctg tgacagagga tgagtctctg cagagcctga aggccagaat ccaacaggac  1080
acgggcatcc cagaggagga ccaggagctg ctgcaggaag cgggcctggc gttgatcccc  1140
gataagcctg ccactcagtg tatttcagac ggcaagttaa atgagggcca cattggac  1200
atggatcttg ttttttctctt tgacaacagt aaaatcacct atgagactca gatctcccca  1260
cggccccaac ctgaaagtgt cagctgtatc cttcaagagc caagaggaa tctcgccttc  1320
ttccagctga ggaaggtgtg gggacaagtc tggcactcag ctcagaccct gaaggaagat  1380
tgcaaccggc tgcagcaggg acagcgagcc gccatgatga atctcctccg aaacaacagc  1440
tgcctctcca aaatgaagaa ttccatggct tccatgtctc agcagctcaa ggccaagttg  1500
gatttcttca aaaccagcat ccagattgac ctggagaagt acagcgagca aaccgagttt  1560
gggatcacat cagataaact gctgctggcc tggagggaaa tggagcaggc tgtggagctc  1620
tgtgggcggg agaacgaagt gaaactcctg gtagaacgga tgatggctct gcagaccgac  1680
```

```
attgtggact tacagaggag ccccatgggc cggaagcagg ggggaacgct ggacgaccta    1740
gaggagcaag caaggagct gtacaggaga ctaaggaaa aacctcgaga ccagcgaact     1800
gagggtgaca gtcaggaaat ggtacggctg ctgcttcagg caattcagag cttcgagaag    1860
aaagtgcgag tgatctatac gcagctcagt aaaactgtgg tttgcaagca gaaggcgctg    1920
gaactgttgc ccaaggtgga agaggtggtg agcttaatga atgaggatga gaagactgtt    1980
gtccggctgc aggagaagcg gcagaaggag ctctggaatc tcctgaagat tgcttgtagc    2040
aaggtccgtg gtcctgtcgc tggagccccg gatgccatga atgccgctcg acttgcccag    2100
cctgggcagc tgatggctca gcccgccacg gccgccaacg ccttacctga gccagccaag    2160
aaggctgaag aactggtggc tgaagcacat aacctctgca ccctgctaga aaatgccata    2220
caggacactg tgagggaaca agaccagagt ttcacggccc tagactggag ctggttacag    2280
acggaagaag aagagcacag ctgcctggag caggcctca                          2319

SEQ ID NO: 7          moltype = AA  length = 768
FEATURE               Location/Qualifiers
REGION                1..768
                      note = IKKalpha inhibiting mutant
source                1..768
                      mol_type = protein
                      organism = synthetic construct
SEQUENCE: 7
HHHHGDYKDD DDKGDIEGRG HMTMERPPGL RPGAGGPWEM RERLGTGGFG NVCLYQHREL     60
DLKIAIMSCR LELSTKNRER WCHEIQIMKK LNHANVVKAC DVPEELNILI HDVPLLAMEY    120
CSGGDLRKLL NKPENCCGLK ESQILSLLSD IGSGIRYLHE NKIIHRDLKP ENIVLQDVGG    180
KIIHKIIDLG YAKDVDQGSL CTSFVGTLQY LAPELFENKP YTATVDYWSF GTMVFECIAG    240
YRPFLHHLQP FTWHEKIKKK DPKCIFACEE MSGEVRFSSH LPQPNSLCSL IVEPMENWLQ    300
LMLNWDPQQR GGPVDLTLKQ PRCFVLMDHI LNLKIVHILN MTSAKIISFL LPPDESLHSL    360
QSRIERETGI NTGSQELLSE TGISLDPRKP ASQCVLDGVR GCDSYMVYLF DKSKTVYEGP    420
FASRSLSDCV NYIVQDSKIQ LPIIQLRKAW AEAVHYVSGL KEDYSRLFQG QRAAMLSLLR    480
YNANLTKMKN TLISASQQLK AKLEFFHKSI QLDLERYSEQ MTYGISSEKM LKAWKEMEEK    540
AIHYAEVGVI GYLEDQIMSL HAEIMELQKS PYGRRQGDLM ESLEQRAIDL YKQLKHRPSD    600
HSYSDSTEMV KIIVHTVQSQ DRVLKELFGH LSKLLGCKQK IIDLLPKVEV ALSNIKEADN    660
TVMFMQGKRQ KEIWHLLKIA CTQAAARALV GAALEGAVAP QAAAWLPPAA AEHDHALACV    720
VAPQDGEAAA QMIEENLNCL GHLAAIIHEA NEEQGNSMMN LDWSWLTE                 768

SEQ ID NO: 8          moltype = DNA  length = 2238
FEATURE               Location/Qualifiers
misc_feature          1..2238
                      note = IKKalpha inhibiting mutant
source                1..2238
                      mol_type = other DNA
                      organism = synthetic construct
SEQUENCE: 8
atggagcggc ccccgggggct gcggccgggc gcgggcgggc cctgggagat gcgggagcgg    60
ctgggcaccg gcggcttcgg gaacgtctgt ctgtaccagc atcgggaact tgatctcaaa   120
atagcaatta tgtcttgtcg cctagagcta agtaccaaaa acagagaacg atggtgccat   180
gaaatccaga ttatgaagaa gttgaaccat gccaatgttg taaaggcctg tgatgttcct   240
gaagaattga atattttgat tcatgatgtg cctcttctag caatgaata ctgttctgga    300
ggagatctcc gaaagctgct caacaaacca gaaaattgtt gtggacttaa agaaagccag   360
atactttctt tactaagtga tataggggtct gggattcgat atttgcatga aaacaaaatt   420
atacatcgag atctaaaacc tgaaaacata gttcttcagg atgttggtgg aaagataata   480
cataaaataa ttgatctggg atatgccaaa gatgttgatc aaggaagtct gtgtacatct   540
tttgtgggaa cactgcagta tctgccccca gagctctttg agaataagcc ttacacagcc   600
actgttgatt attggagctt tgggaccatg gtatttgaat gtattgctgg atataggcct   660
tttttgcatc atctgcagcc atttacctgg catgagaaga ttaagaagaa ggatccaaag   720
tgtatatttg catgtgaaga gatgtcacga gaagttcggt ttagtagcca tttacctcaa   780
ccaaatagcc tttgtagttt aatagtagaa cccatggaaa actggctaca gttgatgttg   840
aattgggacc ctcagcagag aggaggacct gttgaccctta ctttgaagca gccaagatgt   900
tttgtattaa tggatcacat tttgaatttg aagatagtac acatcctaaa tatgacttct   960
gcaaagataa tttcttttct gttaccacct gatgaaagtc ttcattcatt acagtctcgt  1020
attgagcgtg aaactggaat aaatactggt tctcaagaac ttctttcaga gacaggaatt  1080
tctctggatc ctcggaaacc agcctctcaa tgtgttctag atggagttag aggctgtgat  1140
agctatatgg tttatttgtt tgataaaagt aaaactgtat atgaagggcc atttgcttcc  1200
agaagtttat ctgattgtgt aaattatatt gtacaggaca gcaaaataca gcttccaatt  1260
atacagctgc gtaaagcgtg ggctgaagca gtgcactatg tgtctggact aaaagaagac  1320
tatagcaggc tctttcaggg acaaagggca gcaatgttaa gtcttcttag atataatgct  1380
aacttaacaa aaatgaagaa cactttgatc tcagcatcac aacaactgaa agctaaattg  1440
gagttttttc acaaaagcat tcagcttgac ttggagagat acagcgagca gatgacgtat  1500
gggatatctt cagaaaaaat gctaaaagca tggaaagaaa tggaagaaaa ggccatccac  1560
tatgctgagg ttggtgtcat tggataccta ggagatcaga ttatgtcttt gcatgctgaa  1620
atcatggagc tacagaagag ccccatggaa gacgtcagg gagacttgat ggaatctctg   1680
gaacagcgtg ccattgatct atataagcag ttaaaacaca gaccttcaga tcactcctac  1740
agtgacagca cagagatggt gaaaatcatt gtgcacactg tgcagagtca ggaccgtgtg  1800
ctcaaggagc tgtttggtca tttgagcaag ttgttgggct gtaagcagaa gattattgat  1860
ctactccta aggtgaaagt ggccctcagt aatatcaaag aagctgacaa tactgtcatg  1920
ttcatgcagg gaaaaggca gaaagaaatc tggcatctcc ttaaaattgc ctgtacacag  1980
gccgctgccc gcgcccttgt gggagccgct ctggaaggtg cagtggcccc acaggccgcc  2040
gcatggctgc cccctgctgc cgcagaacac gatcacgctc tggcctgtgt ggtggctcct  2100
caagatgggg aggctgccgc acaaatgatc gaagaaaatt tgaactgcct tggccacttg  2160
gccgctatta ttcacgaggc aaatgaggaa cagggcaata gtatgatgaa tcttgattgg  2220
```

```
SEQ ID NO: 9          moltype = AA  length = 779
FEATURE               Location/Qualifiers
REGION                1..779
                      note = IKKbeta inhibiting mutant
source                1..779
                      mol_type = protein
                      organism = synthetic construct
SEQUENCE: 9
SHHHHHGDYK DDDDKGDIEG RGHMSWSPSL TTQTCGAWEM KERLGTGGFG NVIRWHNQET    60
GEQIAIMQCR QELSPRNRER WCLEIQIMRR LTHPNVVAAR DVPEGMQNLA PNDLPLLAME   120
YCQGGDLRKY LNQFENCCGL REGAILTLLS DIASALRYLH ENRIIHRDLK PENIVLQQGE   180
QRLIHKIIDL GYAKELDQGS LCTSFVGTLQ YLAPELLEQQ KYTVTVDYWS FGTLAFECIT   240
GFRPFLPNWQ PVQWHSKVRQ KSEVDIVVSE DLNGTVKFSS SLPYPNNLNS VLAERLEKWL   300
QLMLMWHPRQ RGTDPTYGPN GCFKALDDIL NLKLVHILNM VTGTIHTYPV TEDESLQSLK   360
ARIQQDTGIP EEDQELLQEA GLALIPDKPA TQCISDGKLN EGHTLDMDLV FLFDNSKITY   420
ETQISPRPQP ESVSCILQEP KRNLAFFQLR KVWGQVWHSI QTLKEDCNRL QQGQRAAMMN   480
LLRNNSCLSK MKNSMASMSQ QLKAKLDFFK TSIQIDLEKY SEQTEFGITS DKLLLAWREM   540
EQAVELCGRE NEVKLLVERM MALQTDIVDL QRSPMGRKQG GTLDDLEEQA RELYRRLREK   600
PRDQRTEGDS QEMVRLLLQA IQSFEKKVRV IYTQLSKTVV CKQKALELLP KVEEVVSLMN   660
EDEKTVVRLQ EKRQKELWNL LKIACSKVRG PVAGAPDAMN AARLAQPGQL MAQPATAANA   720
LPEPAKKAEE LVAEAHNLCT LLENAIQDTV REQDQSFTAL DWSWLQTEEE EHSCLEQAS    779

SEQ ID NO: 10         moltype = AA  length = 2271
FEATURE               Location/Qualifiers
REGION                1..2271
                      note = IKKbeta inhibiting mutant
source                1..2271
                      mol_type = protein
                      organism = synthetic construct
SEQUENCE: 10
ATGAGCTGGT CACCTTCCCT GACAACGCAG ACATGCGGGG CCTGGGAAAT GAAAGAGCGC    60
CTTGGGACAG GGGGATTTGG AAATGTCATC CGATGGCACA ATCAGGAAAC AGGTGAGCAG   120
ATTGCCATCA TGCAGTGCCG GCAGGAGCTC AGCCCCCGGA ACCGAGAGCG GTGGTGCCTG   180
GAGATCCAGA TCATGAGAAG GCTGACCCAC CCCAATGTGG TGGCTGCCCG AGATGTCCCT   240
GAGGGGATGC AGAACTTGGC GCCCAATGAC CTGCCCCTGC TGGCCATGGA GTACTGCCAA   300
GGAGGAGATC TCCGGAAGTA CCTGAACCAG TTTGAGAACT GCTGTGGTCT GCGGGAAGGT   360
GCCATCCTCA CCTTGCTGAG TGACATTGCC TCTGCGCTTA GATACCTTCA TGAAAACAGA   420
ATCATCCATC GGGATCTAAA GCCAGAAAAC ATCGTCCTGC AGCAAGGAGA ACAGAGGTTA   480
ATACACAAAA TTATTGACCT AGGATATGCC AAGGAGCTGG ATCAGGGCAG TCTTTGCACA   540
TCATTCGTGG GGACCCTGCA GTACCTGGCC CCAGAGCTAC TGGAGCAGCA GAAGTACACA   600
GTGACCGTCG ACTACTGGAG CTTCGGCACC CTGGCCTTTG AGTGCATCAC GGGCTTCCGG   660
CCCTTCCTCC CCAACTGGCA GCCCGTGCAG TGGCATTCAA AAGTGCGGCA GAAGAGTGAG   720
GTGGACATTG TTGTTAGCGA AGACTTGAAT GGAACGGTGA AGTTTTCAAG CTCTTTACCC   780
TACCCCAATA ATCTTAACAG TGTCCTGGCT GAGCGACTGG AGAAGTGGCT GCAACTGATG   840
CTGATGTGGC ACCCCCGACA GAGGGGCACG GATCCCACGT ATGGGCCCAA TGGCTGCTTC   900
AAGGCCCTGG ATGACATCTT AAACTTAAAG CTGGTTCATA TCTTGAACAT GGTCACGGGC   960
ACCATCCACA CCTACCCTGT GACAGAGGAT GAGAGTCTGC AGAGCTTGAA GGCCAGAATC  1020
CAACAGGACA CGGGCATCCC AGAGGAGGAC CAGGAGCTGC TGCAGGAAGC GGGCCTGGCG  1080
TTGATCCCCG ATAAGCCTGC CACTCAGTGT ATTTCAGACG GCAAGTTAAA TGAGGGCCAC  1140
ACATTGGACA TGGATCTTGT TTTTCTCTTT GACAACAGTA AAATCACCTA TGAGACTCAG  1200
ATCTCCCCAC GGCCCCAACC TGAAAGTGTC AGCTGTATCC TTCAAGAGCC AAGAGGAAT   1260
CTCGCCTTCT TCCAGCTGAG GAAGGTGTGG GGCCAGGTCT GGCACAGCAT CCAGACCCTG  1320
AAGGAAGATT GCAACCGGCT GCAGCAGGGA CAGCGAGCCG CATGATGAA TCTCCTCCGA   1380
AACAACAGCT GCCTCTCCAA AATGAAGAAT TCCATGGCTT CCATGTCTCA GCAGCTCAAG  1440
GCCAAGTTGG ATTTCTTCAA AACCAGCATC CAGATTGACC TGGAGAAGTA CAGCGAGCAA  1500
ACCGAGTTTG GATCACATC AGATAAACTG CTGCTGGCCT GGAGGGAAAT GGAGCAGGCT   1560
GTGGAGCTCT GTGGGCGGGA GAACGAAGTG AAACTCCTGG TAGAACGGAT GATGGCTCTG  1620
CAGACCGACA TTGTGGACTT ACAGAGGAGC CCCATGGGCC GGAAGCAGGG GGGAACGCTG  1680
GACGACCTAG AGGAGCAAGC AAGGGAGCTG TACAGGAGAC TAAGGGAAAA ACCTCGAGAC  1740
CAGCGAACTG AGGGTGACAG TCAGGAAATG GTACGGCTGC TGCTTCAGGC AATTCAGAGC  1800
TTCGAGAAGA AAGTGCGAGT GATCTATACG CAGCTCAGTA AAACTGTGGT TTGCAAGCAG  1860
AAGGCGCTGG AACTGTTGCC CAAGGTGGAA GAGGTGGTGA GCTTAATGAA TGAGGATGAA  1920
AAGACTGTTG TCCGGCTGCA GGAGAAGCGG CAGAAGGAGC TCTGGAATCT CCTGAAGATT  1980
GCTTGTAGCA AGGTCCGTGG TCCTGTCGCT GGAGCCCCGG ATGCCATGAA TGCCGCTCGA  2040
CTTGCCCAGC CTGGGCAGCT GATGGCTCAG CCCGCCACGG CCGCCAACGC CTTACCTGAG  2100
CCAGCCAAGA AGGCTGAAGA ACTGGTGGCT GAAGCACATA ACCTCTGCAC CCTGCTAGAA  2160
AATGCCATAC AGGACACTGT GAGGGAACAA GACCAGAGTT TCACGGCCCT AGACTGGAGC  2220
TGGTTACAGA CGGAAGAAGA AGAGCACAGC TGCCTGGAGC AGGCCTCATG A            2271
```